US010835750B2

(12) United States Patent
Gross

(10) Patent No.: US 10,835,750 B2
(45) Date of Patent: *Nov. 17, 2020

(54) PROSTHETIC AORTIC VALVE PACING SYSTEM

(71) Applicant: RAINBOW MEDICAL LTD., Herzeliya (IL)

(72) Inventor: Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/734,798

(22) Filed: Jan. 6, 2020

(65) Prior Publication Data

US 2020/0139121 A1 May 7, 2020

Related U.S. Application Data

(63) Continuation-in-part of application No. 15/864,661, filed on Jan. 8, 2018, now Pat. No. 10,543,083.

(30) Foreign Application Priority Data

Jan. 7, 2019 (EP) .................................. 19150581

(51) Int. Cl.
*A61F 2/24* (2006.01)
*A61N 1/36* (2006.01)
(Continued)

(52) U.S. Cl.
CPC .......... *A61N 1/3629* (2017.08); *A61F 2/2418* (2013.01); *A61N 1/37223* (2013.01);
(Continued)

(58) Field of Classification Search
CPC .. A61N 1/3629; A61N 1/37512; A61N 1/362; A61F 2/24; A61F 2/2475; A61F 2/2409; A61F 2/2427
See application file for complete search history.

(56) References Cited

U.S. PATENT DOCUMENTS 4,256,094 A  3/1981 Kapp et al.
5,487,760 A  1/1996 Villafana
(Continued)

FOREIGN PATENT DOCUMENTS

EP  3 508 113 A1  7/2019
FR  3034650  10/2016
(Continued)

OTHER PUBLICATIONS

"Pacing at the Bundle of His," Medtronic, Inc., Minneapolis, MN, USA (Oct. 2017).
(Continued)

*Primary Examiner* — Alvin J Stewart
(74) *Attorney, Agent, or Firm* — Sughrue Mion, PLLC

(57) ABSTRACT

A valve prosthesis system is provided, which includes a prosthetic aortic valve and a non-implantable unit. The prosthetic aortic valve which includes a plurality of prosthetic leaflets; a frame; a cathode and an anode, which are mechanically coupled to the frame; and a prosthetic-valve coil, which is in non-wireless electrical communication with the cathode and the anode. The non-implantable unit includes an energy-transmission coil; and non-implantable control circuitry, which is configured to drive the cathode and the anode to apply a pacing signal and to set parameters of the pacing signal, by wirelessly transferring energy from the energy-transmission coil to the prosthetic-valve coil by inductive coupling. Other embodiments are also described.

22 Claims, 7 Drawing Sheets

(51) Int. Cl.
*A61N 1/362* (2006.01)
*A61N 1/375* (2006.01)
*A61N 1/372* (2006.01)

(52) U.S. Cl.
CPC ..... *A61N 1/37512* (2017.08); *A61N 1/37518* (2017.08); *A61F 2210/0014* (2013.01)

(56) References Cited

U.S. PATENT DOCUMENTS

| | | | |
|---|---|---|---|
| 6,030,335 | A | 2/2000 | Franchi |
| 6,030,336 | A | 2/2000 | Franchi |
| 6,050,932 | A | 4/2000 | Franchi |
| 7,643,879 | B2 | 1/2010 | Shuros et al. |
| 7,914,569 | B2 | 3/2011 | Nguyen et al. |
| 8,092,365 | B2 | 1/2012 | Rinderknecht et al. |
| 9,005,106 | B2 | 4/2015 | Gross et al. |
| 9,326,854 | B2 | 5/2016 | Casley et al. |
| 9,526,637 | B2 | 12/2016 | Dagan et al. |
| 9,662,211 | B2 | 5/2017 | Hodson et al. |
| 9,737,264 | B2 | 8/2017 | Braido et al. |
| 9,808,201 | B2 | 11/2017 | Braido et al. |
| 10,543,083 | B2 * | 1/2020 | Gross ................ A61N 1/3787 |
| 2003/0032853 | A1 | 2/2003 | Korakianitis et al. |
| 2004/0024285 | A1 | 2/2004 | Muckter |
| 2004/0097784 | A1 | 5/2004 | Peters et al. |
| 2004/0111006 | A1 | 6/2004 | Alferness et al. |
| 2005/0049696 | A1 | 3/2005 | Siess et al. |
| 2008/0077016 | A1 | 3/2008 | Sparks et al. |
| 2010/0197994 | A1 | 8/2010 | Mehmanesh |
| 2011/0071351 | A1 | 3/2011 | Sperling |
| 2011/0137370 | A1 | 6/2011 | Gross et al. |
| 2011/0196482 | A1 | 8/2011 | Forsell |
| 2012/0245678 | A1 | 9/2012 | Solem |
| 2012/0296382 | A1 | 11/2012 | Shuros et al. |
| 2013/0138205 | A1 | 5/2013 | Kushwaha et al. |
| 2013/0297009 | A1 | 11/2013 | Chalekian et al. |
| 2014/0066895 | A1 | 3/2014 | Kipperman |
| 2014/0081154 | A1 | 3/2014 | Toth |
| 2014/0180391 | A1 | 6/2014 | Dagan et al. |
| 2014/0275720 | A1 | 9/2014 | Ferrari |
| 2015/0128684 | A1 | 5/2015 | Hodson et al. |
| 2016/0045165 | A1 | 2/2016 | Braido et al. |
| 2016/0045316 | A1 | 2/2016 | Braido et al. |
| 2016/0144091 | A1 | 5/2016 | Breedon et al. |
| 2016/0278951 | A1 | 9/2016 | Dagan et al. |
| 2017/0100527 | A1 | 4/2017 | Schwammenthal et al. |
| 2017/0258585 | A1 | 9/2017 | Marquez et al. |
| 2017/0266433 | A1 | 9/2017 | Daniels et al. |
| 2019/0076588 | A1 | 3/2019 | Ochsner et al. |
| 2019/0209302 | A1 | 7/2019 | Gross |

FOREIGN PATENT DOCUMENTS

| | | |
|---|---|---|
| WO | 2013/035092 | 3/2013 |
| WO | 2014/043235 | 3/2014 |
| WO | 2016/157183 | 10/2016 |

OTHER PUBLICATIONS

"Medtronic Evolut™ PRO System brochure," Medtronic, Inc., Minneapolis, MN, USA (Mar. 2017).

"Medtronic CoreValve™ System Instructions for Use," Medtronic, Inc., Minneapolis, MN, USA (2014).

An Office Action dated Apr. 11, 2019, which issued during the prosecution of U.S. Appl. No. 15/864,661.

European Search Report dated May 17, 2019 which issued during the prosecution of Applicant's European App No. 19150581.7.

Jobanputra Y et al., "Rapid Ventricular Pacing During Transcatheter Valve Procedures Using an Internal Device and Programmer: A Demonstration of Feasibility," Journal of the American College of Cardiology, vol. 71, Issue 11 Supplement, Mar. 2018.

* cited by examiner

PROSTHETIC AORTIC VALVE PACING SYSTEM

CROSS-REFERENCE TO RELATED APPLICATIONS

The present application (a) is a continuation-in-part of U.S. application Ser. No. 15/864,661, filed Jan. 8, 2018, now U.S. Pat. No. 10,543,083, and (b) claims foreign priority to European Application 19150581.7, filed Jan. 7, 2019, which published as European Patent Application Publication EP 3 508 113 A1. All of the above-referenced applications are assigned to the assignee of the present application and incorporated herein by reference.

(The above-mentioned European Application 19150581.7 claims foreign priority to the above-mentioned U.S. application Ser. No. 15/864,661.)

FIELD OF THE APPLICATION

The present invention relates generally to surgical implants and systems, and specifically to prosthetic aortic valves and systems.

BACKGROUND OF THE APPLICATION

Aortic heart valve replacement may be necessary to treat valve regurgitation or stenotic calcification of the leaflets. In percutaneous transluminal delivery techniques, a prosthetic aortic valve is compressed for delivery in a catheter and advanced through the descending aorta to the heart, where the prosthetic valve is deployed in the aortic valve annulus. New-onset cardiac conduction disturbances are common after transcatheter aortic valve implantation (TAVI). The most common complication is left bundle branch block (LBBB).

U.S. Pat. No. 7,914,569 to Nguyen et al., which is incorporated herein by reference, describes a heart valve prosthesis having a self-expanding multi-level frame that supports a valve body comprising a skirt and plurality of coapting leaflets. The frame transitions between a contracted delivery configuration that enables percutaneous transluminal delivery, and an expanded deployed configuration having an asymmetric hourglass shape. The valve body skirt and leaflets are constructed so that the center of coaptation may be selected to reduce horizontal forces applied to the commissures of the valve, and to efficiently distribute and transmit forces along the leaflets and to the frame. Alternatively, the valve body may be used as a surgically implantable replacement valve prosthesis.

SUMMARY OF THE APPLICATION

Some embodiments of the present invention provide a prosthetic aortic valve, which comprises a plurality of prosthetic leaflets, a frame, and one or more electrodes coupled to the frame. The frame is shaped so as to define an upstream inflow portion; a downstream outflow portion; and a constriction portion, which is axially between the upstream inflow portion and the downstream outflow portion. The prosthetic leaflets are coupled to the constriction portion. When the prosthetic aortic valve is in an expanded fully-deployed configuration: free edges of the prosthetic leaflets face toward the downstream outflow portion, and a ring-shaped longitudinal border between the downstream outflow portion and the constriction portion is defined by a downstream-most point of the frame to which the prosthetic leaflets are coupled. The prosthetic aortic valve further comprises a prosthetic-valve coil, which is in non-wireless electrical communication with the one or more electrodes, and which is coupled to the frame no more than 1 mm upstream of the ring-shaped longitudinal border, such as axially along the downstream outflow portion.

In some embodiments of the present invention, a valve prosthesis system is provided, which includes a prosthetic aortic valve and a non-implantable unit. The prosthetic aortic valve which includes a plurality of prosthetic leaflets; a frame; a cathode and an anode, which are mechanically coupled to the frame; and a prosthetic-valve coil, which is in non-wireless electrical communication with the cathode and the anode. The non-implantable unit includes an energy-transmission coil; and non-implantable control circuitry, which is configured to drive the cathode and the anode to apply a pacing signal and to set parameters of the pacing signal, by wirelessly transferring energy from the energy-transmission coil to the prosthetic-valve coil by inductive coupling.

There is therefore provided, in accordance with an Inventive concept 1 of the present invention, a method of assembling an electronic prosthetic aortic valve, the method including:

inserting an electronics component into a valve component, the electronics component including one or more electrodes and a prosthetic-valve coil, and the valve component including a frame and prosthetic leaflets coupled to the frame; and coupling the electronics component to the valve component.

Inventive concept 2. The method according to Inventive concept 1, wherein coupling the electronics component to the valve component includes:

coupling a first portion of the electronics component to an inner surface of the frame; and coupling a second portion of the electronics component to an external surface of the frame.

Inventive concept 3. The method according to Inventive concept 2, wherein the first portion of the electronics component includes the prosthetic-valve coil and one of the one or more electrodes, and wherein the second portion of the electronics component includes a cathode the one or more electrodes.

Inventive concept 4. The method according to Inventive concept 3, wherein the electronics component further includes prosthetic-aortic-valve control circuitry, and wherein the first portion of the electronic component includes the prosthetic-aortic-valve control circuitry.

Inventive concept 5. The method according to Inventive concept 4, wherein the electronics component further includes an elongate insulated electrical conductor that electrically couples the cathode to the prosthetic-aortic-valve control circuitry, and wherein coupling the electronics component to the valve component includes coupling the electronics. component to the, valve, component such that the conductor passes from inside to outside the frame.

Inventive concept 6. The method according to Inventive concept 5, wherein the valve component further includes a skirt, and wherein coupling the electronics component to the valve component includes coupling the electronics. component to the valve component such that the conductor passes from inside to outside the frame through the skirt.

Inventive concept 7. The method according to any one of inventive concepts 1-6, wherein coupling the electronics component to the valve component includes stitching the electronics component to the valve component.

Inventive concept 8. The method according to Inventive concept 7, wherein the valve component further includes a skirt, and wherein coupling the electronics component to the valve component includes stitching the electronics component to the. skirt.

Inventive concept 9. The method. according to any one of Inventive concepts 1-3, wherein the frame is shaped so as to define: (1) an upstream inflow portion, (2) a downstream outflow portion, and (3) a constriction portion, which is axially between the upstream inflow portion and the downstream outflow portion, wherein the prosthetic leaflets are coupled to the constriction portion, and wherein the prosthetic aortic valve is configured such that when in an expanded configuration: (A) free edges of the prosthetic leaflets face toward the downstream outflow portion, and (B) a ring-shaped longitudinal border between the downstream outflow portion and the constriction portion is defined by a downstream-most point of the frame to which the prosthetic leaflets are coupled, wherein the prosthetic-valve coil is in non-wireless electrical communication with the one or more electrodes, and wherein coupling the electronics component to the valve component comprises coupling the electronics component to the valve component such that the prosthetic-valve coil is coupled to the frame no more than 1 mm upstream of the ring-shaped longitudinal border.

Inventive concept 10. The method according to Inventive concept 9, wherein coupling the, electronics component to the valve component comprises coupling the electronics component to the valve component such that the prosthetic-valve coil is disposed axially along the downstream outflow portion.

Inventive concept 11. The method according to Inventive concept 9, wherein coupling the electronics component to the valve component comprises coupling the electronics component to the valve component such that at least one of the one or more electrodes is coupled to the upstream inflow portion of the frame.

Inventive concept 12. The method according to Inventive concept 11, wherein the prosthetic aortic valve is configured such that when the prosthetic aortic valve is in the expanded configuration the frame has an inflow end at the upstream inflow portion and a downstream outflow end at the downstream outflow portion, and an axial length, measured between the inflow end and the downstream outflow end, and wherein coupling the electronics component to the valve component comprises coupling the electronics component to the valve component such that at least one of the one or more electrodes is coupled to the upstream inflow portion within a distance from the inflow end, the distance equal to 10% of the axial length of the frame.

There is further provided, in accordance with an Inventive concept 13 of the present invention, apparatus including a prosthetic aortic valve, which includes:

(a) a plurality of prosthetic leaflets;
(b) a frame, which is shaped so as to define:
(1) an upstream inflow portion,
(2) a downstream outflow portion, and
(3) a constriction portion, which is axially between the upstream inflow portion and the downstream out portion, wherein the prosthetic leaflets are coupled to the constriction portion, and wherein when the prosthetic aortic valve is in an expanded fully-deployed configuration: (A) free edges of the prosthetic leaflets face toward the downstream outflow portion, and (B) a ring-shaped longitudinal border between the downstream outflow portion and the constriction portion is defined by a downstream-most point of the frame to which the prosthetic leaflets are coupled;

(c) one or more electrodes coupled to the frame; and
(d) a prosthetic-valve coil, which in non-wireless electrical communication with the one or more electrodes, and which is coupled to the frame no more than 1 mm upstream of the ring-shaped longitudinal border.

Inventive concept 14. The apparatus according to Inventive concept 13, wherein the prosthetic-valve coil is disposed axially along the downstream outflow portion.

Inventive concept 15. The apparatus according to Inventive concept 13, wherein at least one of the one or more electrodes is coupled to the upstream inflow portion of the frame.

Inventive concept 16. The apparatus according to Inventive concept 15, wherein when the prosthetic aortic valve is in the expanded fully-deployed configuration:

the frame has an inflow end at the upstream inflow portion and a downstream outflow end at the downstream outflow portion, and an axial length, measured between the inflow end and the downstream outflow end, and at least one of the one or more electrodes is coupled to the upstream inflow portion within a distance from the inflow end, the distance equal to 10% of the axial length of the frame.

Inventive concept 17. A valve prosthesis system comprising the prosthetic aortic valve according to Inventive concept 13, the valve prosthesis system further including an external unit, which includes:

an external-unit coil; and
external-unit control circuitry, which is configured to drive the external-unit coil to wirelessly transfer energy, by inductive coupling, to the prosthetic-valve coil when the prosthetic aortic valve is in the expanded fully-deployed configuration.

Inventive concept 18. The valve prosthesis system according to Inventive concept 17, wherein the external-unit control circuitry is configured to drive the one or more electrodes to apply a pacing signal.

Inventive concept 19. The valve, prosthesis system according to Inventive concept 17, wherein the external unit includes a collar configured to be worn around a patient's neck, and the external-unit coil is incorporated into the collar.

Inventive concept 20. The valve prosthesis system. according to Inventive concept 13, wherein the prosthetic aortic valve further includes prosthetic-aortic-valve control circuitry, which is coupled to the frame and which is in non-wireless electrical communication with the one or more electrodes, and wherein the prosthetic-valve coil is in non-wireless electrical communication with the prosthetic-aortic-valve control circuitry, such that the prosthetic-valve coil is in non-wireless electrical communication with the one or more electrodes via the prosthetic-aortic-valve control circuitry.

Inventive concept 21. The valve prosthesis system according to Inventive concept 20, wherein the prosthetic-aortic-valve control circuitry is configured to apply pacing.

Inventive concept 22. The valve prosthesis system according to Inventive concept 20, wherein the one or more electrodes include a cathode that is coupled to the upstream inflow portion of the frame, and wherein the prosthetic-aortic-valve control circuitry is configured to drive the cathode to apply a cathodic current.

Inventive concept 23. The valve prosthesis system according to Inventive concept 22, wherein the prosthetic aortic valve further includes a skirt coupled to an external surface of the upstream inflow portion of the frame, and wherein the cathode is disposed on an external surface of the skirt.

Inventive concept 24. The valve prosthesis system according to Inventive concept 20, wherein the prosthetic leaflets are coupled to the frame at at least first and second commissures that are located at respective first and second angular locations around the frame separated by a first angular offset around the frame when the prosthetic aortic valve is in the expanded fully-deployed configuration, and wherein the prosthetic-aortic-valve control circuitry is. coupled to the frame at a third angular location around the frame that is separated from the first angular location by a second angular offset that equals between 40% and 60% of the first angular offset when the prosthetic aortic valve is in the expanded fully-deployed configuration.

Inventive concept 25. The valve prosthesis system according to Inventive concept 20, wherein the prosthetic-aortic-valve control circuitry is coupled to the frame inside the frame.

Inventive concept 26. The valve prosthesis system according to Inventive concept 20, wherein the prosthetic-aortic-valve control circuitry is stitched to the frame.

Inventive concept 27. The valve prosthesis system according to Inventive concept 20, wherein the prosthetic aortic valve further includes a skirt coupled to an external surface of the upstream inflow portion of the frame, and wherein the prosthetic-aortic-valve control circuitry is stitched to the skirt.

Inventive concept 28. The valve, prosthesis system according to Inventive concept 20, wherein the prosthetic-aortic-valve control circuitry is configured to (a) use the one or more electrodes to sense a cardiac signal, and (b) drive the prosthetic-valve coil to transmit a wireless signal indicative of the sensed cardiac signal.

Inventive concept 29. The valve prosthesis system according to Inventive concept 20, wherein the prosthetic aortic valve includes an electronic implant, which includes:

the prosthetic-aortic-valve control circuitry; and a multi-laver protective coating, which includes the following lavers in the following order:

a first inner aluminum oxide (AlOx) film layer deposited on the circuitry; and a second parylene layer deposited on the first inner AlOx film layer, wherein the prosthetic-aortic-valve control circuitry is not encased in a case.

There is still further provided, in accordance with an Inventive concept 30 of the present invention, apparatus including an electronic implant, which includes:

circuitry; and a multi-layer protective coating, which includes the following layers in the following order:

a first inner aluminum oxide (AlOx) film layer deposited on the circuitry; and a second parylene, layer deposited on the first inner AlOx film layer, wherein the circuitry is not encased in a case.

Inventive concept 31. The apparatus according to Inventive concept 30, wherein the multi-layer protective coating further includes a third layer disposed on the second parylene layer, the third layer having a thickness of between 100 and 200 microns, and configured to provide mechanical protection for the circuitry.

Inventive concept 32. The apparatus according to Inventive concept 31, wherein the third layer includes a material selected from the group consisting of: silicone and PTFE.

Inventive concept 33. The apparatus according to Inventive concept 31, wherein the third layer is cast onto the second parylene layer.

Inventive concept 34. The apparatus according to Inventive concept 31, wherein the multi-layer protective coating further includes a fourth outer parylene layer deposited on the third layer.

Inventive concept 35. The apparatus according to Inventive concept 30, further including a prosthetic aortic valve, which includes:

a frame;

a plurality of prosthetic leaflets coupled to the frame;

one or more electrodes coupled to the frame; and a prosthetic-valve coil coupled co the frame, wherein the electronic implant is coupled to the frame and is in non-wireless electrical communication with the one or more electrodes, and wherein the prosthetic-valve coil is in non-wireless electrical communication with the circuitry, such that the prosthetic-valve coil is in non-wireless electrical communication with the one, or more electrodes via the circuitry.

There is additionally provided, in accordance with an Inventive concept 36 of the present invention, a method of manufacturing an electronic implant, the method including:

depositing a first inner aluminum oxide (AlOx) film layer on circuitry of the electronic implant; and depositing a second parylene layer on the first inner AlOx film laver, so as to form a multi-layer protective coating with the first inner AlOx film layer, wherein manufacturing the electronic implant does not include encasing the circuitry in a case.

Inventive concept 37. The method according to Inventive concept 36, further including disposing a third layer on the second parylene layer, the third layer having a thickness of between 100 and 200 microns, and configured to provide mechanical protection for the circuitry.

Inventive concept 38. The method according to Inventive concept 37, wherein the third layer includes a material selected from the group consisting of: silicone and PTFE.

Inventive concept 39. The method according to Inventive concept 37, wherein disposing the third layer includes casting the third layer onto the second parylene layer.

Inventive concept 40. The method according to Inventive concept 37, further including depositing a fourth outer parylene layer on the third layer.

There is yet additionally provided, in accordance with an Inventive concept 41 of the present invention, apparatus including a prosthetic aortic valve, which includes:

(a) a plurality of prosthetic leaflets;
(b) a frame, which is shaped so as to define:
  (1) an upstream inflow portion,
  (2) a downstream outflow portion, and
  (3) a constriction portion, which is axially between the upstream inflow portion and the downstream outflow portion, wherein the prosthetic leaflets are coupled to the constriction portion, and wherein when the prosthetic aortic valve is in an expanded fully-deployed configuration: (A) free edges of the prosthetic leaflets face toward the downstream outflow portion, and (B) a ring-shaped longitudinal border between the downstream outflow portion and the constriction portion is defined by a downstream-most point of the frame to which the prosthetic leaflets are coupled;

(c) one or more electrodes coupled to the upstream inflow portion of the frame; and (d) a prosthetic-valve coil, which is in non-wireless electrical communication with the one or more electrodes.

Inventive concept 42. The apparatus according to Inventive concept 41, wherein when the prosthetic aortic valve is in the expanded fully-deployed configuration:

the frame has an inflow end at the upstream inflow portion and a downstream outflow end at the downstream outflow portion, and an axial length, measured between the inflow end and the downstream outflow end, and at least one of the one or more electrodes is coupled to the upstream inflow portion within a distance from the inflow end, the distance equal to 10% of the axial length of the frame.

Inventive concept 43. The apparatus according to Inventive concept 41, wherein the prosthetic aortic valve further includes prosthetic-aortic-valve control circuitry, which is coupled to the frame and which is in non-wireless electrical communication with the one or more electrodes, and wherein the prosthetic-valve coil is in non-wireless electrical communication with the prosthetic-aortic-valve control circuitry, such that the prosthetic-valve coil is in non-wireless electrical communication with the one or more electrodes via the prosthetic-aortic-valve control circuitry.

Inventive concept 44. The apparatus according to Inventive concept 43, wherein the prosthetic-artic-valve control circuitry is configured to apply pacing.

Inventive concept 45. The apparatus according to Inventive concept 43, wherein the one or more electrodes include a cathode that is coupled to the upstream inflow portion of the frame, and wherein the prosthetic-aortic-valve control circuitry is configured to drive the cathode to apply a cathodic current.

Inventive concept 46. The apparatus according to Inventive concept 45, wherein the prosthetic aortic valve further includes a skirt coupled to an external surface of the upstream inflow portion of the frame, and wherein the cathode is disposed on an external surface of the skirt.

There is also provided, in accordance with an Inventive concept 47 of the present invention, a method of assembling an electronic prosthetic aortic valve, the method including:

inserting an electronics component into a valve component, the electronics component including one or more electrodes and a prosthetic-valve coil, and the valve component including a frame and prosthetic leaflets coupled to the frame; and coupling the electronics component. to the valve component.

Inventive concept 48. The method according to Inventive concept 47, wherein coupling the electronics component to the valve component includes:

coupling a first portion of the electronics component to an inner surface of the frame; and coupling a second portion of the electronics component to an external surface of the frame.

Inventive concept 49. The method according to Inventive concept 48, wherein the first portion of the electronics component includes the prosthetic-valve coil and one of the one or more electrodes, and wherein the second portion of the electronics component includes a cathode of the one or more electrodes.

Inventive concept 50. The method according to inventive concept 49, wherein the electronics component further includes prosthetic-aortic-valve control circuitry, and wherein the first portion of the electronic component includes the prosthetic-aortic-valve control circuitry.

Inventive concept 51. The method according to Inventive concept 50, wherein the electronics component further includes an elongate insulated electrical conductor that electrically couples the cathode to the prosthetic-aortic-valve control circuitry, and wherein coupling the electronics component to the valve component includes coupling the electronics component to the valve component such that the conductor passes from inside to outside the frame.

Inventive concept 52. The method according to Inventive concept 51, wherein the valve component further includes a skirt, and wherein coupling the electronics component to the valve component includes coupling the electronics component to the valve component such that the conductor passes from inside to outside the frame through the skirt.

Inventive concept 53. The method according to inventive concept 47, wherein coupling the electronics component to the valve component includes stitching the electronics component to the valve component Inventive concept 54. The method according to inventive concept 47, wherein the valve component further includes a skirt, and wherein coupling the electronics component to the valve component includes stitching the electronics component to the skirt.

There is further provided, in accordance with an Inventive concept 55 of the present invention, apparatus including a valve prosthesis system including:

(a) a delivery system, which includes:
a delivery tube;
a delivery-system coil, which is coupled to the delivery tube at a distal site of the delivery tube;
one or more wires, which pass along the delivery tube; and
delivery-system control circuitry, which is in electrical communication with the delivery-system coil via the one or more wires; and (b) a prosthetic aortic valve, which includes:
a frame;
a plurality of prosthetic leaflets coupled to the frame;
one or more electrodes coupled to the frame; and
a prosthetic-valve coil coupled to the frame and in non-wireless electrical communication with the one or more electrodes, wherein the prosthetic aortic valve is (i) removably disposable in the delivery tube in a compressed delivery configuration and (ii) configured to assume:

(A) a partially-expanded partially-deployed configuration upon being partially released from a distal end of the delivery tube such that (1) at least one of the one or more electrodes is positioned outside the delivery tube, and (2) the prosthetic-valve coil is compressed within the delivery tube, and (B) an expanded fully-deployed configuration upon being fully released from the distal end of the delivery tube, and wherein the delivery-system control circuitry is configured to drive the delivery-system coil to wirelessly transfer energy, by inductive coupling, to the prosthetic-valve coil at least when the prosthetic aortic valve is in the partially-deployed configuration.

Inventive concept 56. The apparatus according to Inventive concept 55, the valve prosthesis system further includes an external unit, which includes:
an external-unit coil; and
external-unit control circuitry, which is configured to drive the external-unit coil to wirelessly transfer energy, by inductive coupling, to the prosthetic-valve coil when the prosthetic aortic valve is in the expanded fully-deployed configuration.

Inventive concept 57. The apparatus according to Inventive concept 56, wherein the external-unit control circuitry is configured to begin driving the external-unit coil to wirelessly transfer the energy only after the prosthetic aortic valve is in the expanded fully-deployed configuration.

Inventive concept 58. The apparatus according to Inventive concept 55, wherein the delivery-system control circuitry is configured to cease driving the delivery-system coil to wirelessly transfer the energy when the prosthetic aortic valve assumes the expanded fully-deployed configuration upon being fully released from the distal end of the delivery tube.

Inventive concept 59. The apparatus according to Inventive concept 55,
wherein the frame is shaped so as to define:
an upstream inflow portion,
a downstream outflow portion, and
a constriction portion, which is axially between the upstream inflow portion and the downstream outflow portion, wherein the prosthetic leaflets are coupled to the constriction portion such that free edges of the prosthetic leaflets face toward the downstream outflow portion when the prosthetic aortic valve is in the expanded fully-deployed configuration, and
wherein the prosthetic-valve coil is disposed axially along the downstream outflow portion.

Inventive concept 60. The apparatus according to Inventive concept 59, wherein the prosthetic-valve coil is not disposed axially along the constriction portion and is not disposed axially along the upstream inflow portion.

Inventive concept 61. The apparatus according to Inventive concept 59, wherein at least one of the one or more electrodes is coupled to the upstream inflow portion of the frame.

Inventive concept 62. The apparatus according to Inventive concept 61, wherein when the prosthetic aortic valve is in the expanded fully-deployed configuration:
the frame has an inflow end at the upstream inflow portion and a downstream outflow end at the downstream outflow portion, and an axial length, measured between the inflow end and the downstream outflow end, and
at least one of the one or more electrodes is coupled to the upstream inflow portion within a distance from the inflow end, the distance equal to 10% of the axial length of the frame.

Inventive concept 63. The apparatus according to Inventive concept 55,
wherein the prosthetic aortic valve further includes prosthetic-aortic-valve control circuitry, which is coupled to the frame and which is in non-wireless electrical communication with the one or more electrodes, and
wherein the prosthetic-valve coil is in non-wireless electrical communication with the prosthetic-aortic-valve control circuitry, such that the prosthetic-valve coil is in non-wireless electrical communication with the one or more electrodes via the prosthetic-aortic-valve control circuitry.

Inventive concept 64. The apparatus according to Inventive concept 63,
wherein the frame is shaped so as to define:
an upstream inflow portion,
a downstream outflow portion, and
a constriction portion, which is axially between the upstream inflow portion and the downstream outflow portion, wherein the prosthetic leaflets are coupled to the constriction portion such that free edges of the prosthetic leaflets face toward the downstream outflow portion when the prosthetic aortic valve is in the expanded fully-deployed configuration,
wherein the one or more electrodes include a cathode that is coupled to the upstream inflow portion of the frame, and
wherein the prosthetic-aortic-valve control circuitry is configured to drive the cathode to apply a cathodic current.

Inventive concept 65. The apparatus according to Inventive concept 64, wherein the prosthetic aortic valve further includes a skirt coupled to an external surface of the upstream inflow portion of the frame, and wherein the cathode is disposed on an external surface of the skirt.

Inventive concept 66. The apparatus according to Inventive concept 63,
wherein the prosthetic leaflets are coupled to the frame at at least first and second commissures that are located at respective first and second angular locations around the frame separated by a first angular offset around the frame when the prosthetic aortic valve is in the expanded fully-deployed configuration, and
wherein the prosthetic-aortic-valve control circuitry is coupled to the frame at a third angular location around the frame that is separated from the first angular location by a second angular offset that equals between 40% and 60% of the first angular offset when the prosthetic aortic valve is in the expanded fully-deployed configuration.

Inventive concept 67. The apparatus according to Inventive concept 63, wherein the prosthetic-aortic-valve control circuitry is coupled to the frame inside the frame.

Inventive concept 68. The apparatus according to Inventive concept 63, wherein the prosthetic-aortic-valve control circuitry is configured to (a) use the one or more electrodes to sense a cardiac signal, and (b) drive the prosthetic-valve coil to transmit a wireless signal indicative of the sensed cardiac signal.

Inventive concept 69. The apparatus according to Inventive concept 63, wherein the prosthetic-aortic-valve control circuitry is configured co drive the one or more electrodes to apply rapid ventricular pacing.

Inventive concept 70. The apparatus according to Inventive concept 55, wherein the delivery-system control circuitry is configured to drive the one or more electrodes, via the delivery-system coil and the prosthetic-valve coil, to apply rapid ventricular pacing.

There is still further provided, in accordance with an Inventive concept 71 of the present invention, a method including:
advancing, through vasculature of a patient, a delivery tube of a delivery system of a valve prosthesis system including, until a distal end of the delivery tube is disposed in an ascending aorta of the patient, while a prosthetic aortic valve of the valve prosthesis system is removably disposed in the delivery tube in a compressed delivery configuration, wherein the prosthetic aortic valve includes (a) a frame, (b) a plurality of prosthetic leaflets coupled to the frame, (c) one or more electrodes coupled to the frame, and (d) a prosthetic-valve coil coupled to the frame and in non-wireless electrical communication with the one or more electrodes;
partially releasing the prosthetic aortic valve from the distal end of the delivery tube such that the prosthetic aortic valve assumes a partially-expanded partially-deployed configuration, in which (a) at least one of one or more electrodes is positioned outside the delivery tube, and (b) the prosthetic-valve coil is compressed within the delivery tube;

thereafter, activating delivery-system control circuitry to drive a delivery-system coil to wirelessly transfer energy, by inductive coupling, to the prosthetic-valve coil at least when the prosthetic aortic valve is in the partially-deployed configuration, wherein the delivery-system coil is coupled to the delivery tube at a distal site of the delivery tube, and wherein the delivery-system control circuitry is in electrical communication with the delivery-system coil via one or more wires that pass along the delivery tube; and thereafter, fully releasing the prosthetic aortic valve from the distal end of the delivery tube such that the prosthetic aortic valve assumes an expanded fully-deployed configuration.

Inventive concept 72. The method according to Inventive concept 71, further including, after fully releasing the prosthetic aortic valve from the distal end of the delivery tube, activating external-unit control circuitry of an external unit to drive an external-unit coil to wirelessly transfer energy, by inductive coupling, to the prosthetic-valve coil when the prosthetic aortic valve is in the expanded fully-deployed configuration.

Inventive concept 73. The method according to Inventive concept 71, wherein the delivery-system control circuitry is configured to cease driving the delivery-system coil to wirelessly transfer the energy when the prosthetic aortic valve assumes the expended fully-deployed configuration upon being fully released from the distal end of the delivery tube.

Inventive concept 74. The method according to Inventive concept 71,
wherein the frame is shaped so as to define:
an upstream inflow portion,
a downstream outflow portion, and
a constriction portion, which a axially between the upstream inflow portion and the downstream outflow portion, wherein the prosthetic leaflets are couple to the constriction portion such that free edges of the prosthetic leaflets face toward the downstream outflow portion when the prosthetic aortic valve is in the expanded fully-deployed configuration, and
wherein the, prosthetic-valve coil is disposed axially along the downstream outflow portion.

Inventive concept 75. The method according to Inventive concept 74, wherein the prosthetic-valve coil is not disposed axially along the constriction portion or the upstream inflow portion.

Inventive concept 76. The method according to Inventive concept 74, wherein at least one of the one or more electrodes is coupled to the upstream inflow portion of the frame.

Inventive concept 77. The method according to inventive concept 76, wherein when the prosthetic aortic valve is in the expanded fully-deployed configuration:
the frame has an inflow end at the upstream inflow portion and a downstream outflow end at the downstream outflow portion, and an axial length, measured between the inflow end and the downstream outflow end, and
at least one of the one or more electrodes is coupled to the upstream inflow portion within a distance from the inflow end, the distance equal to 10% of the axial length of the frame.

Inventive concept 78. The method according to Inventive concept 71,
wherein the prosthetic aortic valve further includes prosthetic-aortic-valve control circuitry, which is coupled to the frame and which is in non-wireless electrical communication with the one or more electrodes, and
wherein the prosthetic-valve coil is in non-wireless electrical communication with the prosthetic-aortic-valve control circuitry, such that the prosthetic-valve coil is in non-wireless electrical communication with the one or more electrodes via the prosthetic-aortic-valve control circuitry.

Inventive concept 79. The method according to Inventive concept 78,
wherein the frame is shaped so as to define:
an upstream inflow portion,
a downstream outflow portion, and
a constriction portion, which is axially between the upstream inflow portion and the downstream outflow portion, wherein the prosthetic leaflets are coupled to the constriction portion such that free edges of the prosthetic leaflets face toward the downstream outflow portion when the prosthetic aortic valve is in the expanded fully-deployed configuration,
wherein the one or more electrodes include a cathode that is coupled to the upstream inflow portion of the frame, and
wherein the prosthetic-aortic-valve control circuitry is configured to drive the cathode to apply a cathodic current.

Inventive concept 80. The method according to inventive concept 78,
wherein the prosthetic leaflets are coupled to the frame at at least first and second commissures that are located at respective first and second angular locations around the frame separated by a first angular offset around the frame when the prosthetic aortic valve is in the expanded fully-deployed configuration, and
wherein the prosthetic-aortic-valve control circuitry is coupled to the frame at a third angular location around the frame that is separated from the first angular location by a second angular offset that equals between 40% and 60% of the first angular offset when the prosthetic aortic valve is in the expanded fully-deployed configuration.

Inventive concept 81. The method according to Inventive concept 78, wherein the prosthetic-aortic-valve control circuitry is coupled to the frame inside the frame.

Inventive concept 82. The method according to Inventive concept 78, wherein the prosthetic-aortic-valve control circuitry is configured to (a) use the one or more electrodes to sense a cardiac signal, and (b) drive the prosthetic-valve coil to transmit a wireless signal indicative of the sensed cardiac signal.

Inventive concept 83. The method according to inventive concept 78, wherein the prosthetic-aortic-valve control circuitry is configured to drive the one or more electrodes to apply rapid ventricular pacing.

Inventive concept 84. The method according to Inventive concept 71, wherein activating the delivery-system control circuitry includes activating the delivery-system control circuitry to drive the one or more electrodes, via the delivery-system coil and the prosthetic-valve coil, to apply rapid ventricular pacing.

There is still further provided, in accordance with an Inventive concept 85 of the present invention, a valve prosthesis system comprising:
(i) a prosthetic aortic valve, which comprises:
(a) a plurality of prosthetic leaflets;
(b) a frame;
(c) a cathode and an anode, which are mechanically coupled to the frame; and (d) a prosthetic-valve coil, which is in non-wireless electrical communication with the cathode and the anode; and (ii) a non-implantable unit, which comprises:

(a) an energy-transmission coil; and (b) non-implantable control circuitry, which is configured to drive the cathode and the anode to apply a pacing, signal and to set parameters of the pacing signal, by wirelessly transferring energy from the energy-transmission coil to the prosthetic-valve coil by inductive coupling.

Inventive concept 86. The valve prosthesis system according to Inventive concept 85, wherein the prosthetic aortic valve comprises one or more elongate insulated electrical conductors, which directly couple the prosthetic-valve coil in the non-wireless electrical communication with the cathode and the anode.

Inventive concept 87. The valve prosthesis system according to Inventive concept 85, wherein respective ends of the prosthetic-valve coil are in the non-wireless electrical communication with the cathode and the anode.

Inventive concept 88. The valve prosthesis system according to Inventive concept 85, wherein respective non-electrically-insulated end portions of the prosthetic-valve coil define the cathode and the anode.

Inventive concept 89. The valve prosthesis system according to Inventive concept 85, wherein the non-implantable control circuitry is configured to set an amplitude of the pacing signal by modulating an amplitude of the energy wirelessly transferred from the energy-transmission coil to the prosthetic-valve coil.

Inventive concept 90. The valve prosthesis system according to Inventive concept 85, wherein the non-implantable control circuitry is configured to drive the cathode and the anode to (a) begin application of each pulse of the pacing signal by beginning wirelessly transferring energy from the energy-transmission coil to the prosthetic-valve coil, and (b) conclude the application of each pulse of the pacing signal by ceasing wirelessly transferring energy from the energy-transmission coil to the prosthetic-valve coil.

Inventive concept 91. The valve prosthesis system according to Inventive concept 85, wherein the frame is shaped so as to define: (1) an upstream inflow portion, (2) a downstream outflow portion, and (3) a constriction portion, which is axially between the upstream inflow portion and the downstream outflow portion, wherein the prosthetic leaflets are coupled to the constriction portion, and wherein the cathode is mechanically coupled to the upstream inflow portion of the frame.

Inventive concept 92. The valve prosthesis system according to Inventive concept 91, wherein the prosthetic-valve coil is disposed axially along the downstream outflow portion of the frame.

Inventive concept 93. The valve prosthesis system according to Inventive concept 85, wherein the cathode and the anode are disposed on the frame such that there is at least 15 mm between the cathode and the anode, when the prosthetic aortic valve is in an expanded fully-deployed configuration, the 15 mm measured along a central longitudinal axis of the frame when in the expanded fully-deployed configuration.

Inventive concept 94. The valve prosthesis system according to Inventive concept 85, wherein the non-implantable unit is an external unit, which is configured to be disposed outside a body of a subject in which the prosthetic aortic valve is disposed.

Inventive concept 95. The valve prosthesis system according to Inventive concept 85, wherein the non-implantable unit is a delivery system, which further comprises a delivery tube, and one or more wires, which pass along the delivery tube, wherein the non-implantable control circuitry is delivery-system control circuitry, which is in electrical communication with the delivery-system coil via the one or more wires, and wherein the energy-transmission coil is coupled to the delivery tube at a distal site of the delivery tube.

Inventive concept 96. The valve prosthesis system according to Inventive concept 95, wherein the delivery-system control circuitry is configured to drive the cathode and the anode to apply rapid ventricular pacing, by wirelessly transferring the energy from the energy-transmission coil to the prosthetic-valve coil by inductive coupling.

Inventive concept 97. The valve prosthesis system according to Inventive concept 95, wherein the prosthetic aortic valve is (i) removably disposable in the delivery tube in a compressed delivery configuration and (ii) configured to assume:

(A) a partially-expanded partially-deployed configuration upon being partially released from a distal end of the delivery tube such that (1) at least the cathode is positioned on the delivery tube, and (2) the prosthetic-valve coil is compressed within the delivery tube, and (B) an expanded fully-deployed configuration upon being fully released from the distal end of the delivery tube, and wherein the delivery-system control circuitry is configured to drive the cathode and the anode to apply the pacing signal and to set the parameters of the pacing signal, by wirelessly transferring the energy from the energy-transmission coil to the prosthetic-valve coil at least when the prosthetic aortic valve is in the partially-deployed configuration.

Inventive concept 98. The valve prosthesis system according to Inventive concept 97, further comprising an external unit, which is configured to be disposed outside a body of a subject in which the prosthetic aortic valve is disposed, and which comprises:

an external-unit coil; and external unit control circuitry, which is configured to drive the external-unit coil to drive the cathode and the anode to apply the pacing signal and to set the parameters of the pacing signal, by wirelessly transferring energy, by inductive coupling, to the prosthetic-valve coil when the prosthetic aortic valve is in the expanded fully-deployed configuration.

There is additionally provided, in accordance with an Inventive concept 99 of the present invention, a method comprising:

deploying, via vasculature of a patient, a prosthetic aortic valve of a valve prosthesis system in an aortic valve annulus, the prosthetic aortic valve including (a) a plurality of prosthetic leaflets, (b) a frame, (c) a cathode and an anode, which are mechanically coupled to the frame, and (d) a prosthetic-valve coil, which is in non-wireless electrical communication with the cathode and the anode; and activating non-implantable control circuitry of a non-implantable unit of the valve prosthesis system to drive the cathode and the anode to apply a pacing signal and to set parameters of the pacing signal, by wirelessly transferring energy from an energy-transmission coil of the non implantable unit to the prosthetic-valve coil by inductive coupling.

Inventive concept 100. The method according to Inventive concept 99, wherein the prosthetic aortic valve includes one or more elongate insulated electrical conductors, which directly couple the prosthetic-valve coil in the non-wireless electrical communication with the cathode and the anode.

Inventive concept 101. The method according to Inventive concept 99, wherein respective ends of the prosthetic-valve coil are in the non-wireless electrical communication with the cathode and the anode.

Inventive concept 102. The method according to Inventive concept 99, wherein respective non-electrically-insulated end portions of the prosthetic-valve of define the cathode and the anode.

Inventive concept 103. The method according to Inventive concept 99, wherein activating the non-implantable control circuitry to drive the cathode and the anode to apply the pacing signal comprises activating the non-implantable control circuitry to set an amplitude of the pacing signal by modulating an amplitude of the energy wirelessly transferred from the energy-transmission coil to the prosthetic-valve coil.

Inventive concept 104. The method according to Inventive concept 99, wherein activating the non-implantable control circuitry to drive, the cathode and the anode to apply the pacing signal comprises activating the non-implantable control circuitry to drive the cathode and the anode to (a) begin application of each pulse of the pacing signal by beginning wirelessly transferring energy from the energy-transmission coil to the prosthetic-valve coil, and (b) conclude the application of each pulse of the pacing signal by ceasing wirelessly transferring energy from the energy-transmission coil to the prosthetic-valve coil.

Inventive concept 105. The method according to Inventive concept 99, wherein the frame is shaped so as to define: (1) an upstream inflow portion, (2) a downstream outflow portion, and (3) a constriction portion, which is axially between the upstream inflow portion and the downstream outflow portion, wherein the prosthetic leaflets are coupled to the constriction portion, and wherein the cathode is mechanically coupled to the upstream inflow portion of the frame.

Inventive concept 106. The method according to Inventive concept 105, wherein the prosthetic-valve coil is disposed axially along the downstream outflow portion of the frame.

Inventive concept 107. The method according to Inventive concept 99, wherein the cathode and the anode are disposed on the frame such that there is at least 15 mm between the cathode and the anode, when the prosthetic aortic valve is in an expanded fully-deployed configuration, the 15 mm measured along a central longitudinal axis of the frame when in the expanded fully-deployed configuration.

Inventive concept 108. The method according to Inventive concept 99, wherein the non-implantable unit is an external unit, which is disposed outside a body of a subject in which the prosthetic aortic valve is disposed.

Inventive concept 109. The method according to Inventive concept 99, wherein the non-implantable unit is a delivery system of the valve prosthesis system, and the energy-transmission coil is a delivery-system coil that is coupled to a delivery tube of the delivery system at a distal site of the delivery tube, wherein the non-implantable control circuitry is delivery-system control circuitry, which is in electrical communication with the delivery-system coil via one or more wires that pass along the delivery tube, wherein deploying the prosthetic aortic valve comprises:
advancing the delivery tube through the vasculature until a distal end of the delivery tube is disposed in an ascending aorta of the patient, while the prosthetic aortic valve is removably disposed in the delivery tube in a compressed delivery configuration; and
partially releasing the prosthetic aortic valve from the, distal end of the delivery tube such that the prosthetic aortic valve assumes a partially-expanded partially-deployed configuration, in which (a) at least the cathode is positioned outside the delivery tube, and (b) the prosthetic-valve coil is compressed within the delivery tube;

wherein activating the non-implantable control circuitry comprises, after partially releasing the prosthetic aortic valve from the distal end of the delivery tube, activating the delivery-system control circuitry to drive the cathode and the anode to apply the pacing signal and to set the parameters of the pacing signal, by wirelessly transferring energy from the delivery-system coil to the prosthetic-valve coil by inductive coupling at least when the prosthetic aortic valve is in the partially-deployed configuration, and wherein deploying the prosthetic aortic valve further comprises, after activating the delivery-system control circuitry, fully releasing the prosthetic aortic valve from the distal end of the delivery tube such that the prosthetic aortic valve assumes an expanded fully-deployed configuration.

Inventive concept 110. The method according to Inventive concept 109, wherein activating the delivery-system control circuitry comprises activating the delivery-system control circuitry to drive the cathode and the anode to apply rapid ventricular pacing, by wirelessly transferring the energy from the energy-transmission coil to the prosthetic-valve coil by inductive coupling at least when the prosthetic aortic valve in the partially-deployed configuration.

Inventive concept 111. The method according to Inventive concept 109, further comprising, after fully releasing the prosthetic aortic valve from the distal end of the delivery tube, activating external-unit control circuitry of an external unit to drive an external-unit coil of the external unit to drive the cathode and the anode to apply the pacing signal and to set the parameters of the pacing signal, by wirelessly transferring energy, by inductive coupling, to the prosthetic-valve coil when the prosthetic aortic valve is in the expanded fully-deployed configuration, wherein the external unit is disposed outside a body of a subject in which the prosthetic aortic valve is disposed.

Inventive concept 112. The method according to Inventive concept 109, wherein the delivery-system control circuitry is configured to cease driving the delivery-system coil to drive the cathode and the anode when the prosthetic aortic valve assumes the expanded fully deployed configuration upon being fully released from the distal end of the delivery tube.

Inventive concept 113. The method according to Inventive concept 109, wherein partially releasing the prosthetic aortic valve from the distal end of the delivery tube comprises positioning the cathode adjacent to cardiac tissue near the bundle of His.

Inventive concept 114. The method according to Inventive concept 113, wherein positioning the cathode adjacent to the cardiac tissue near the bundle of His comprises rotating the prosthetic aortic valve if necessary during deployment such that the cathode is disposed against the cardiac tissue near the bundle of His.

The present invention will be more fully understood from the following detailed description of embodiments thereof, taken together with the drawings, in which:

DETAILED DESCRIPTION OF APPLICATIONS

Figure 1A:
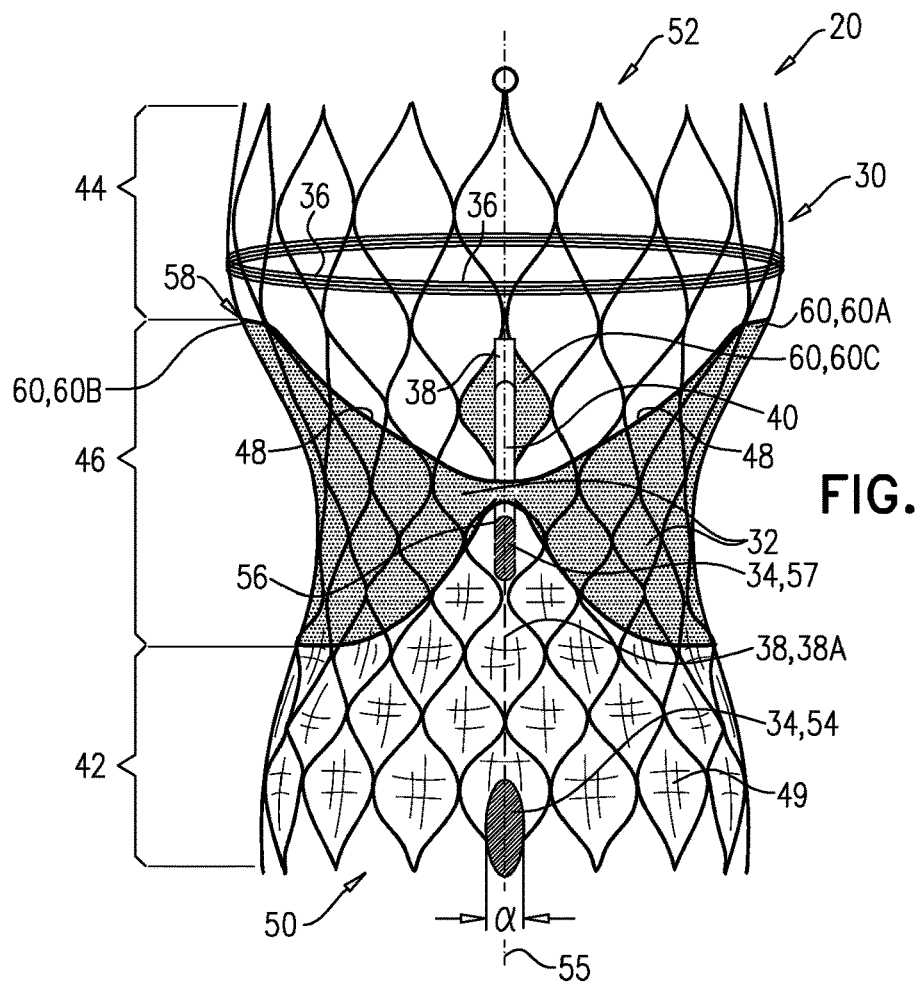
FIGS. 1A and 1B are schematic illustrations of a prosthetic aortic valve, in accordance with an application of the present invention.
Figure 1B:
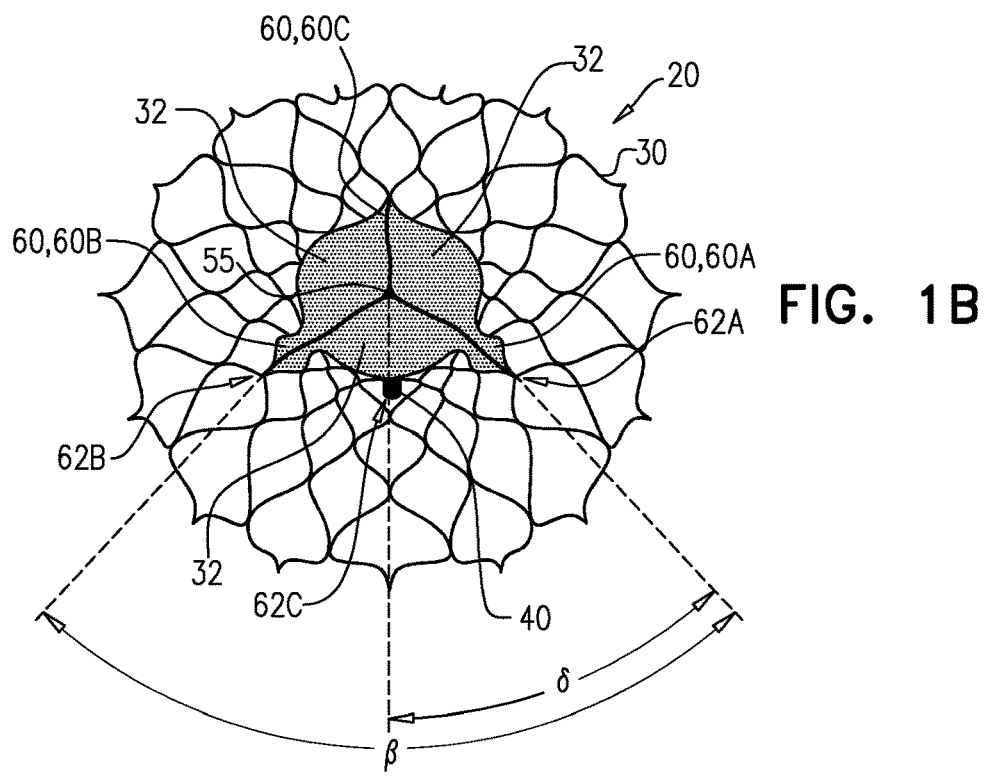

FIGS. 1A and 1B are schematic illustrations of a prosthetic aortic valve, 20, in accordance with an application of the present invention. Prosthetic aortic valve 20 is shown in FIGS. 1A-B in an expanded configuration, which is similar to the expanded fully-deployed configuration described hereinbelow with reference to FIG. 4C, except that in FIGS. 1A-B expansion of prosthetic aortic valve 20 is not limited by anatomy of a patient. FIG. 1B is a view of prosthetic aortic valve 20 from a downstream outflow end 52, as described hereinbelow.

Prosthetic aortic valve 20 comprises:
a frame 30;
a plurality of prosthetic leaflets 32 coupled to frame 30;
one or more electrodes 34 coupled to frame 30; and
a prosthetic-valve coil 36 coupled to frame 20 and in non-wireless electrical communication with the one or more electrodes 34, optionally by one or more elongate insulated electrical conductors 38, e.g., wires.

Frame 30 typically comprises a stent or other structure, which is typically self-expanding, and may be formed by laser cutting or etching a metal alloy tube comprising, for example, stainless steel or a shape memory material such as Nitinol. For some applications, one or more of electrodes 34 are coupled to frame 30 using techniques described in U.S. Pat. No. 9,526,637 to Dagan et al and/or US 2016/0278951 to Dagan et al., both of which are incorporated herein by reference. For some applications, prosthetic-valve coil 36 comprises gold wire, in order to provide low resistance.

For some applications, prosthetic aortic valve 20 further comprises prosthetic-aortic-valve control circuitry 40, which is coupled to frame 30 and which in non-wireless electrical communication with the one or more electrodes 34. In these applications, prosthetic-valve coil 36 is in non-wireless electrical communication with prosthetic-aortic-valve control circuitry 40, such that prosthetic-valve oil 36 is in non-wireless electrical communication with the one or more electrodes 34 via prosthetic-aortic-valve control circuitry 40. One or more of the one or more electrodes 34 may be directly attached in non-wireless electrical communication to prosthetic-aortic-valve control circuitry 40, and/or may be attached in non-wireless electrical communication to prosthetic-aortic-valve control circuitry 40 by the one or more elongate insulated electrical conductors 38. Typically, prosthetic-aortic-valve control circuitry 40 is flexible, and has a thin, linear packaging, and may implement techniques described hereinbelow with reference to FIG. 5. The thinness of control circuitry 40 allows it to be compressed in a delivery tube during deployment of prosthetic aortic valve, 20, without the need to increase the diameter of the delivery tube. In addition, the flexibility of control circuitry 40 prevents damage to the control circuitry when it is crimped when compressed into the delivery tube.

For some applications, frame 30 is shaped so as to define an upstream inflow portion 42, a downstream outflow portion 44, and a constriction portion 46, which axially between upstream inflow portion 42 and downstream outflow portion 44. Prosthetic leaflets 32 are coupled to constriction portion 46 such that free edges 48 of prosthetic leaflets 32 face toward downstream outflow portion 44 when prosthetic aortic valve 20 is in the expanded fully-deployed configuration described hereinbelow with reference to FIG. 4C. Prosthetic leaflets 32 are not coupled to downstream outflow portion 44; therefore, a ring-shaped longitudinal border 58 between downstream outflow portion 44 and constriction portion 46 is defined by a downstream-most point of frame 30 to which prosthetic leaflets 32 are coupled (for example, prosthetic leaflets 32 may be coupled to the downstream-most point of frame 30 at commissures 60, described immediately hereinbelow). (Ring-shaped longitudinal border 58 is at the same longitudinal location around frame 30.) Typically, prosthetic aortic valve 20 further comprises a skirt 49 coupled to upstream inflow portion 42 of frame 30, and prosthetic leaflets 32 are attached along their bases no skirt 49, for example, using sutures or a suitable biocompatible adhesive. Adjoining pairs of leaflets are attached to one another at their lateral ends to form commissures 60, with free edges 48 of the prosthetic leaflets forming coaptation edges that meet one another. Skirt 49 and prosthetic leaflets 32 typically comprise a sheet of animal pericardial tissue, such as porcine pericardial tissue, or synthetic or polymeric material.

For some applications, prosthetic-valve coil 36 is disposed no more than 1 mm upstream of ring-shaped longitudinal border 58 between downstream outflow portion 44 and constriction portion 46, typically axially along downstream outflow portion 44. Such placement allows prosthetic aortic valve 20 to be crimped (compressed) into a delivery tube during deployment of prosthetic aortic valve 20, without requiring a larger-diameter delivery tube to accommodate prosthetic-valve coil 36. This is possible because downstream outflow portion 44 does not include material of prosthetic leaflets 32, and thus can accommodate prosthetic-valve coil 36 without causing downstream outflow portion 44 to have a greater compressed diameter than the other axial portions of prosthetic aortic valve 20. Typically, prosthetic-valve coil 36 is not disposed axially along constriction portion 46 and is not disposed axially along upstream inflow portion 42. In addition, placement of prosthetic-valve coil 36 axially along downstream outflow portion 44 improves transmission efficiency because downstream outflow portion 44 typically has a greater diameter than each of constriction portion 46 and upstream inflow portion 42. In addition, constriction portion 46 typically has a lesser diameter than each of upstream inflow portion 42 and downstream outflow portion 44.

Typically, at least one of the one or more electrodes 34 is coupled to upstream inflow portion 42 of frame 30, such as exactly one of the one or more electrodes 34. For some applications, the one or more electrodes 34 comprise a cathode 54 that is coupled to upstream inflow portion 42 of frame 30, and prosthetic-aortic-valve control circuitry 40 is configured to drive cathode 54 to apply a cathodic current. For some applications, cathode 54 has a lateral dimension (alpha), measured in degrees around frame 30 with respect to a central longitudinal axis 55 of frame 30, of between 10 and 40 degrees, e.g., between 20 and 40 degrees, such as 30 degrees, in order to accommodate rotational misplacement of frame 30 with respect to the bundle of His. Typically, prosthetic aortic valve 20 is deployed using imaging, such as fluoroscopy, and is rotated if necessary during the deployment such that cathode 54 is disposed against tissue of the annulus that is near the bundle of His. For some applications, prosthetic aortic valve 20 comprises a plurality of cathodes 54 (e.g., two or three, or more), which are disposed at a respective plurality of angular locations around frame 30 (e.g., 10-15 degrees apart). After implantation of prosthetic aortic valve 20, the cathode 54 that is has the most accurate angular location is activated to apply a pacing signal and/or sense, either by prosthetic-aortic-valve control circuitry 40 or external control circuitry, such as external-unit control circuitry 104, described hereinbelow with reference to FIG. 4C. Alternatively or additionally, for some applications, cathode 54 has an axial length of at least 10 mm, in order to accommodate axial misplacement of frame 30 with respect to the annulus of the natural aortic valve, and thus with respect to the bundle of His. As used in the present application, including in the claims, an "axial length" is a length of a structure measured along central longitudinal axis 55.

For some applications, cathode 54 has a thickness of between 75 and 125 microns, e.g., about 100 microns, and/or a surface area of at least 2.5 mm2, in order to provide adequate stimulation. For some applications, cathode 54 comprises titanium nitride (TiN). For some applications, skirt 49 is coupled to an external surface of upstream inflow portion 42 of frame 30, and cathode 54 is disposed on an external surface of skirt 49. As used in the present application, including in the claims, the "central longitudinal axis" 55 of frame 30 is the set of all centroids of transverse cross-sectional sections of frame 30 along frame 30. Thus the cross-sectional sections are locally perpendicular to the central longitudinal axis, which runs along frame 30. (For applications in which frame 30 is circular in cross-section, the centroids correspond with the centers of the circular cross-sectional sections.)

For some applications, when prosthetic aortic valve 20 is in the expanded fully-deployed configuration described hereinbelow with reference to FIG. 4C:

frame 30 has an inflow end 50 at upstream inflow portion 42 and downstream outflow end 52 at downstream outflow portion 44, and an axial length, measured between inflow end 50 and downstream outflow end 52, and at least one of (e.g., exactly one of, e.g., cathode 54) the one or more electrodes 34 is coupled to upstream inflow portion 42 within a distance from inflow end 50, the distance equal to 10% of the axial length of frame 30 (the distance is measured (a) along central longitudinal axis 55 of frame 30 when in the expanded fully-deployed configuration, and (b) between inflow end 50 and an upstream-most point of the at least one electrode).

Typically, prosthetic-aortic-valve control circuitry 40 is coupled to frame 30 such that upstream-most point 56 of prosthetic-aortic-valve control circuitry 40 is disposed axially along control fiction portion 44 and/or downstream outflow portion 44 of frame 30.

Typically, prosthetic-aortic-vive control circuitry 40 is coupled to frame 30 inside frame 30, which may prevent friction between prosthetic-aortic-valve control circuitry 40 and delivery tube 72 during deployment of prosthetic aortic valve 20, described hereinbelow with reference to FIGS. 4A-C. It is noted that for applications in which upstream-most point 56 is disposed no more upstream than 1 mm upstream of ring-shaped longitudinal border 58, such as described above, there is generally enough space inside frame 30 to accommodate prosthetic-aortic-valve control circuitry 40.

For some applications, prosthetic leaflets 32 are coupled to frame 30 at at least first and second commissures 60A and 60B of prosthetic aortic valve 20 that are located at respective first and second angular locations 62A and 62B around frame 30. The first and second angular locations 62A and 620 are separated by a first angular offset β (beta) around frame 30 when prosthetic aortic valve 20 is in the expanded fully-deployed configuration described hereinbelow with reference to FIG. 4C. Prosthetic-aortic-valve control circuitry 40 is coupled to frame 30 at a third angular location 62C around frame 30 that is separated from first annular location 62A by a second angular offset δ (delta) that equals between 40% and 60% (e.g., 50%) of the first angular offset β (beta) when prosthetic aortic valve 20 is in the expanded fully-deployed configuration described hereinbelow with reference to FIG. 4C. At the third angular location 62C around frame 30, the frame is more flexible than at the more rigid commissures. As used in the present application, including in the claims, an "angular location" is a location on frame 30 at a particular location around. central longitudinal axis 55, i.e., at a particular "o'clock" with respect to central longitudinal axis 55. (It is noted that a third commissures 60C is shown in FIG. 1A on the far side of the frame, i.e., 180 degrees from circuitry 40.)

Figure 2:
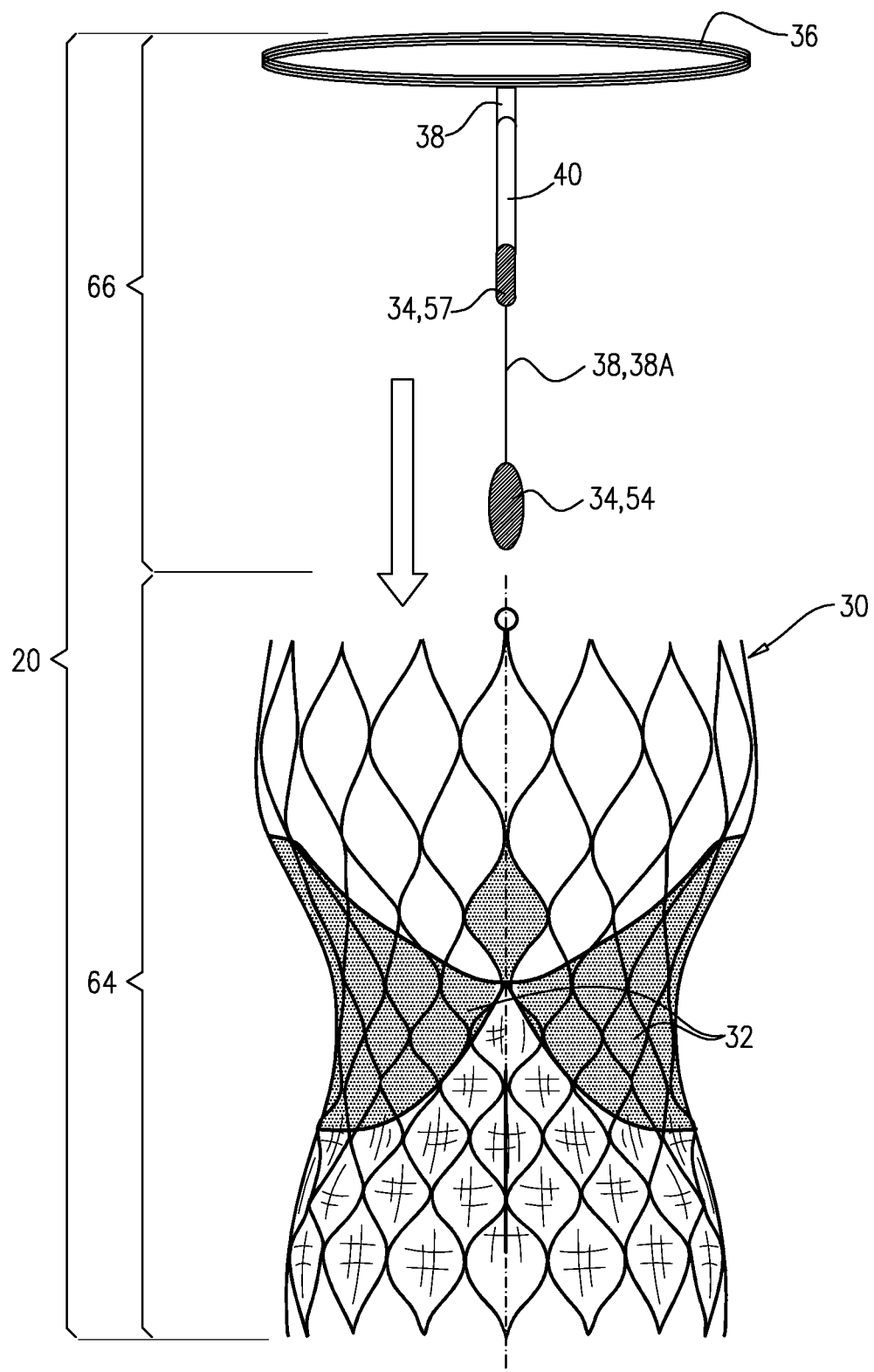
FIG. 2 is a schematic illustration of components of the prosthetic aortic valve of FIGS. 1A-B before complete assembly, in accordance with an application of the present invention.

Reference is now made to FIG. 2, which is a schematic illustration of components of prosthetic aortic valve 20 before complete assembly, in accordance with an application of the present invention. The components comprise a valve component 64 and an electronics component 66. Valve component 64 typically consists of a heart valve prosthesis known in the art, which comprises at least frame 30 and prosthetic leaflets 32. For example, the known heart valve prosthesis may comprise a CoreValve™ Evolut™ R prothesis (Medtronic, Inc., Minneapolis, Minn., USA), a CoreValve™ Evolut™ PRO prosthesis (Medtronic, Inc), a LOTUS Edge™ Aortic Valve (Boston Scientific Corporation, Marlborough, Mass., USA) , or an ACURATE neo™ Aortic Valve (Boston Scientific Corporation). Electronics component 66 comprises at least the one or more electrodes 34 and prosthetic-valve coil 36, and optionally prosthetic-aortic-valve control circuitry 40.

During assembly of prosthetic aortic valve 20, electronics component 66 is inserted into valve component 64. For some applications, a first portion of electronics component 66, such as prosthetic-valve coil 36, prosthetic-aortic-valve control circuitry 40, and one of the one or more electrodes 34, is coupled to an inner surface of frame 30, and a second portion of electronics component 66, such as cathode 54, is coupled to an external surface of frame 30. For example, one 38A of one or more elongate insulated electrical conductors 38 may electrically couple cathode 54 to prosthetic-aortic-valve control circuitry 40, and the conductor 38A may pass from inside to outside frame 30, typically through skirt 49. (Coupling one of the one or more electrodes 34 to the inner surface of frame 30 may expose the electrode to blood of the subject upon implantation of the assembled prosthetic aortic valve 20. Coupling cathode 54 to the external surface of frame 30 may dispose the cathode against tissue, such as tissue of the annulus that is near the bundle of His, upon implantation of the assembled prosthetic aortic valve 20, such as described herein.) Optionally, the components of electronics component 66 may be stitched to frame 30 and/or skirt 49.

For some applications, whether prosthetic-valve coil 36 is coupled to an inner or an external surface of frame 30, prosthetic-valve coil 36 is electrically isolated from frame 30, such as by isolation material (e.g., a sheet of material or a coating) disposed between prosthetic-valve coil 36 and frame 30. For example, the isolation material may comprise a non-conductive polymer.

The above-mentioned assembly of prosthetic aortic valve 20 is typically performed in a manufacturing facility, and thereafter the assembled prosthetic aortic valve 20 is packaged and shipped to a healthcare facility for implantation. The method of assembling prosthetic aortic valve 20 is thus non-surgical.

Figure 3:
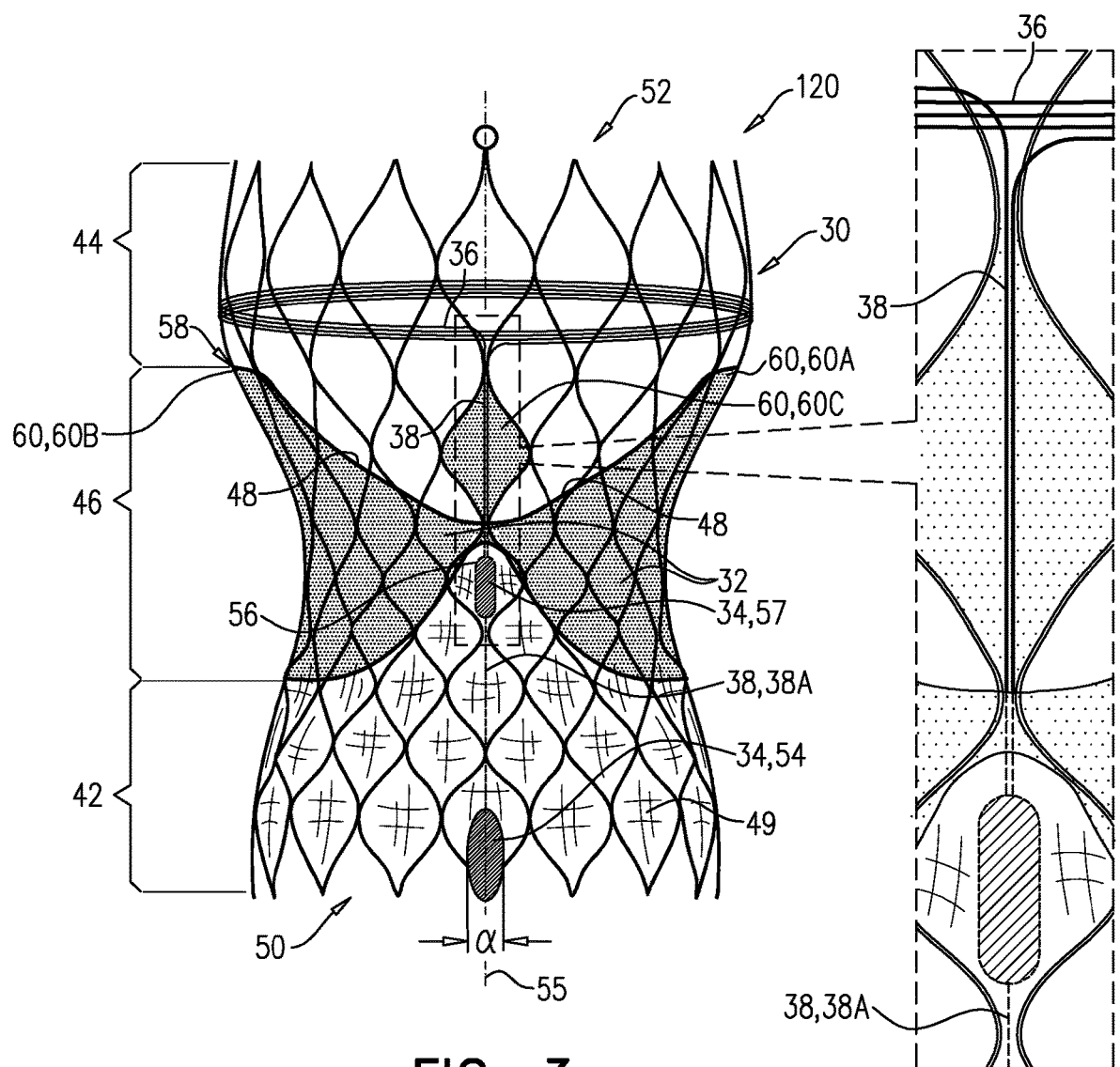
FIG. 3 is a schematic illustration of another aortic valve, in accordance with an application of the present invention.

FIG. 3 is a schematic illustration of a prosthetic aortic valve 120, in accordance with an application of the present invention. Prosthetic aortic valve 120 is shown in FIG. 3 in an expanded configuration, which is similar to the expanded fully-deployed configuration of prosthetic aortic valve 20 described hereinbelow with reference to FIG. 4C, except that in FIG. 3 expansion of prosthetic aortic valve 120 is not limited by anatomy of a patient. Other than as described hereinbelow, prosthetic aortic valve 120 is identical to prosthetic aortic valve 20 described herein with reference to FIGS. 1A-B, 2, and 4A-C, and like reference numerals refer to like parts. Prosthetic aortic valve 120 may be assembled as described hereinabove with reference to FIG. 2 for prosthetic aortic valve 20, mutatis mutandis.

As mentioned hereinbelow with reference to FIG. 4B regarding prosthetic aortic valve 20, for some applications, delivery-system control circuitry 80 is configured to drive the one or more electrodes 34 to apply the rapid ventricular pacing; in this configuration, prosthetic-aortic-valve control circuitry 40, if even provided, is generally passive, i.e., delivery-system control circuitry 80 sets the parameters of the pacing signal. Prosthetic aortic valve 120, shown in FIG. 3, is one implementation of this configuration; unlike the configuration of prosthetic aortic valve 20 illustrated in FIGS. 1A-B, 2, and 4A-C, prosthetic aortic valve 120 does not comprise prosthetic-aortic-valve control circuitry 40.

A valve prosthesis system is provided that comprises (a) prosthetic aortic valve 120 and (b) a non-implantable unit, such as delivery system 70, described hereinbelow with reference to FIGS. 4A-C, or external unit 100, described hereinbelow with reference to FIG. 4C. Non-implantable control circuitry (such as delivery-system control circuitry 80 or external-unit control circuitry 104, as appropriate) is configured to drive cathode 54 and anode 57 to apply a pacing signal and to set parameters of the pacing signal (e.g., to be rapid ventricular pacing), by wirelessly transferring energy from an energy-transmission coil (such as delivery-system coil 74 or external-unit coil 102, as appropriate) to prosthetic-valve coil 36 by inductive coupling.

Optionally, the valve prosthesis system comprises two non-implantable units: (1) delivery system 70, described hereinbelow with reference to FIGS. 4A-C, and (2) external unit 100, described hereinbelow with reference to FIG. 4C, which comprise, respective control circuitry and energy-transmission coils. Delivery-system control circuitry 80 is configured to drive, delivery-system coil 74 to drive cathode 54 and anode 57 to apply the pacing signal and to set the parameters of the pacing signal, by wirelessly transferring energy, by inductive coupling, to prosthetic-valve coil 36 when prosthetic aortic valve 120 at least when prosthetic aortic valve 120 is in the partially-deployed configuration, such as described hereinbelow with reference to FIG. 4B. External-unit control circuitry 104 is configured to drive external-unit coil 102 to drive cathode 54 and anode 57 to apply the pacing signal and to set the parameters of the pacing signal, by wirelessly transferring energy, by inductive coupling, to prosthetic-valve coil 36 when prosthetic aortic valve 120 is in the expanded fully-deployed configuration, such as described hereinbelow with reference to FIG. 4C.

Typically, respective, ends of prosthetic-valve coil 36 are in the non-wireless electrical communication with cathode 54 and anode 57.

For some applications, respective non-electrically-insulated end portions of prosthetic-valve coil 36 define cathode 54 and anode 57. In these applications, prosthetic aortic valve 120 typically does not comprise elongate insulated electrical conductors 38. Instead, respective insulated end portions of prosthetic-valve coil 36 bend away from prosthetic-valve coil 36 along the paths of elongate insulated electrical conductors 30 shown in FIG. 3, such that the respective non-electrically-insulated end portions of prosthetic-valve coil 36 are located at the locations at which cathode 54 and anode 57 are shown in FIG. 3, respectively.

As mentioned above, the non-implantable control circuitry is configured to drive cathode 54 and anode 57 to set parameters of the pacing signal. For example, the non-implantable to control circuitry may be configured to set an amplitude of the pacing signal by modulating an amplitude of the energy wirelessly transferred from the energy-transmission coil to prosthetic-valve coil 36. Alternatively or additionally, for example, the non-implantable control circuitry may be configured to drive cathode 54 and anode 57 to (a) begin application of each pulse of the pacing signal by beginning wirelessly transferring energy from the energy-transmission coil to prosthetic-valve coil 36, and (b) conclude the application of each pulse of the pacing signal by ceasing wirelessly transferring energy from the energy-transmission coil to prosthetic-valve coil 36.

Figure 4A:
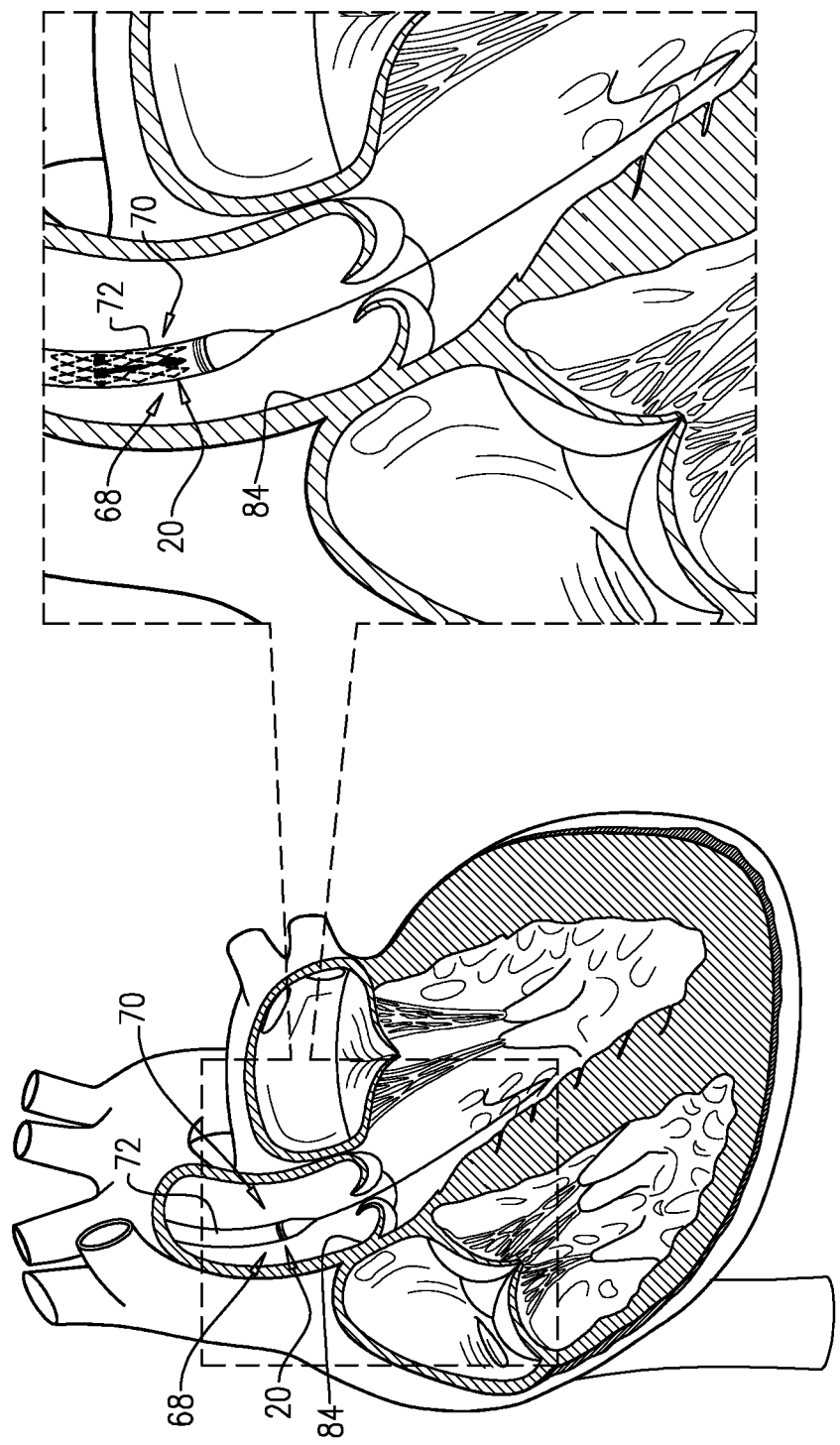
FIGS. 4A-C are schematic illustrations of a valve prosthesis system and a method of using the system, in accordance with respective applications of the present invention.
Figure 4B:
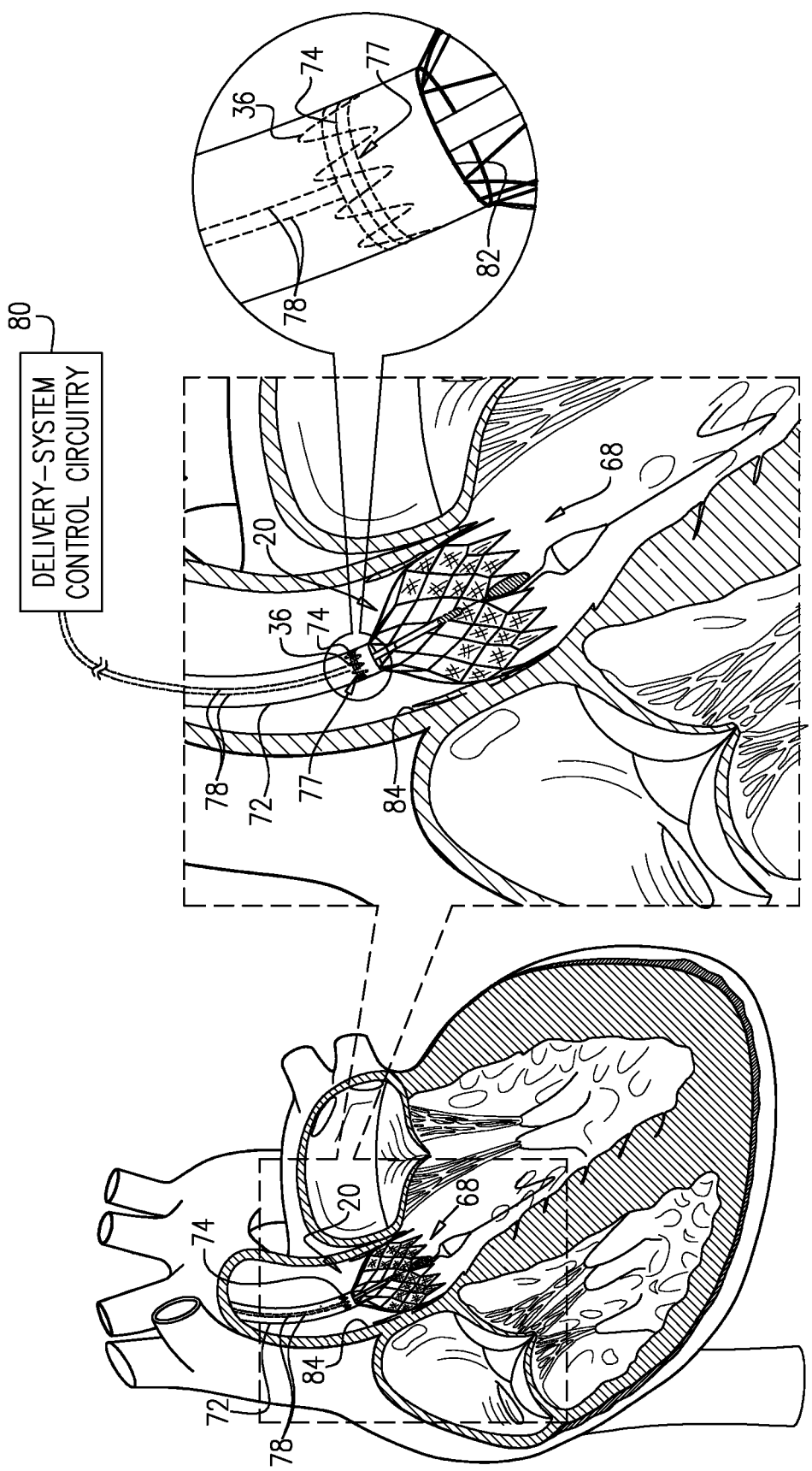
Figure 4C:
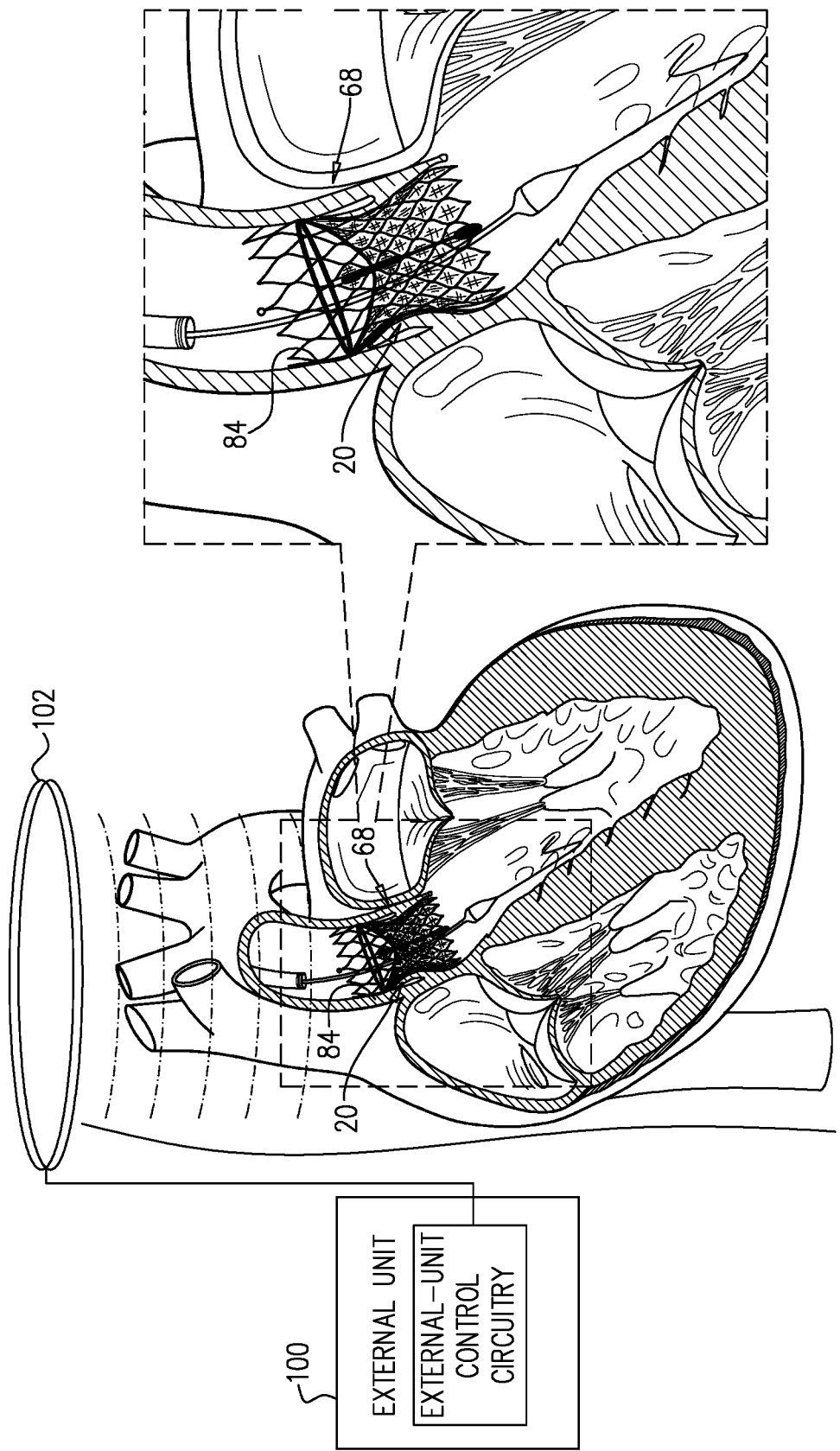

Reference is made to FIGS. 1A-B, 2, and 3, and is additionally made to FIGS. 4A-C, which are schematic illustrations of a valve prosthesis system 68 and a method of using the system, in accordance with respective applications of the present invention. Although the techniques described with reference to FIGS. 4A-C are generally described regarding prosthetic aortic valve 20, the techniques are equally applicable to prosthetic aortic valve 120, mutatis mutandis.

Valve prosthesis system 68 comprises prosthetic aortic valve 20 or prosthetic aortic valve 120 and a delivery system 70.

Delivery system 70 comprises:
- a delivery tube 72;
- a delivery-system coil 74, which is coupled to delivery tube 72 at a distal site 76 of delivery tube 72; for example, a distal-most portion 77 of delivery-system coil 74 may be disposed within 10 mm of a distal end 82 of delivery tube 72;
- one or more wires 78, which pass along delivery tube 72, e.g., attached to an outer or inner surface of delivery tube 72, or embedded in the wall of delivery tube 72; and
- delivery-system control circuitry 80, which is in electrical communication with delivery-system coil 74 via the one or more wires 78.

Delivery-system control circuitry 80 is configured to drive delivery-system coil 74 to wirelessly transfer energy (and, optionally, programming information), by inductive coupling, to prosthetic-valve coil 36 at least when prosthetic aortic valve 20 is in the partially-deployed configuration described hereinbelow with reference to FIG. 4B.

As shown in FIG. 4A, prosthetic aortic valve 20 is removably disposable in delivery tube 72 in a compressed delivery configuration. During an implantation procedure, delivery tube 72 is advanced through vasculature of a patient, until distal end 82 of delivery tube 72 is disposed in an ascending aorta 84 of the patient, while prosthetic aortic valve 20 is removably disposed in delivery tube 72 in the compressed delivery configuration.

As shown in FIG. 4B, prosthetic aortic calve 20 is also configured to assume a partially-expanded partially-deployed configuration upon being partially released from distal end 82 of delivery tube 72 such that (a) at least one of the one or more electrodes 34 is positioned outside delivery tube 72, such as cathode 54, in the vicinity of (e.g., touching) target tissue, such as the natural aortic valve annulus, and (b) prosthetic-valve coil 36 is compressed within delivery tube 72. Typically, delivery-system coil 74 surrounds compressed prosthetic-valve coil 36, which provides high transmission efficiency even though prosthetic-valve coil 36 is still compressed. After prosthetic aortic valve 20 has assumed the partially-expanded partially-deployed configuration, delivery-system control circuitry 80 is activated to drive delivery-system coil 74 to wirelessly transfer energy (and, optionally, programming information), by inductive coupling, to prosthetic-valve coil 36. By contrast, transmission of power from an external coil compressed prosthetic-valve coil 36 would be quite inefficient because of the greater distance between the transmitting and receiving coils and the compression of prosthetic-valve coil 36.

For some applications, prosthetic-aortic-valve control circuitry 40 is configured to drive the one or more electrodes 34 to apply rapid ventricular pacing. Such pacing may temporary reduce left ventricular output, in order to enable more accurate placement of prosthetic aortic valve 20. Alternatively, such as described hereinabove with reference to FIG. 3, delivery-system control circuitry 80 is configured to drive the one or more electrodes 34 to apply the rapid ventricular pacing; in this configuration, prosthetic-aortic-valve control circuitry 40, if even provided, is generally passive, i.e., delivery-system control circuitry 80 sets the parameters of the pacing signal. Alternatively, prosthetic aortic valve 20 is not used for applying rapid ventricular pacing, and may instead be used for applying pacing post-implantation, such as described below, and/or for post-implantation sensing, such as described below.

As described hereinabove with reference to FIGS. 1A-F, for some applications, the one or more electrodes 34 comprise cathode 54 that is coupled to upstream inflow portion 42 of frame 30. When prosthetic aortic valve 20 is in the partially-expanded partially-deployed configuration shown in FIG. 4B, cathode 54 is positioned adjacent to cardiac tissue near the bundle of His, in order to pace the heart by stimulating the cardiac tissue with cathodic current. For some applications, the one or more electrodes further comprise an anode 57, which may be used for bipolar sensing and/or pacing, as known in the art. Typically, cathode 54 and anode 57 are disposed on frame 30 such that there is at least 15 mm between the cathode and the anode, when prosthetic aortic valve 20 is in the expanded fully-deployed configuration described hereinbelow with reference to FIG. 4C (the 15 mm is measured along central longitudinal axis 55 of frame 30 when in the expanded fully-deployed configuration).

As shown in FIG. 4C, prosthetic aortic valve. 20 is also configured to assume an expanded fully-deployed configuration upon being fully released from distal end 82 of delivery tube 72. For some applications, delivery-system control circuitry 80 is configured to cease driving delivery-system coil 74 to wirelessly transfer the energy when prosthetic aortic valve 20 assumes the expanded fully-deployed configuration upon being fully released from distal end 82 of delivery tube 72.

For some applications, as shown in FIG. 4C, valve prosthesis system 68 further comprises an external unit 100, which comprises (a) an external-unit coil 102, and (b) external-unit control circuitry 104, which is configured to drive external-unit coil 102 to wirelessly transfer energy (and, optionally, programming information), by inductive coupling, to prosthetic-valve coil 36 when prosthetic aortic valve 20 is in the expanded fully-deployed configuration. In these applications, after prosthetic aortic valve 20 is fully released from distal end 82 of delivery tube 72, external-unit control circuitry 104 is activated to drive external-unit coil 102 to wirelessly transfer energy (and, optionally, programming information), by inductive coupling, to prosthetic-valve coil 36 when prosthetic aortic valve 20 is in the expanded fully-deployed configuration.

For some applications, external-unit coil 102 is incorporated into a collar configured to be worn around the patient's neck or placed on the patient's chest, such as described in PCT Publication WO 2016/157183 to Dagan et al., which is incorporated herein by reference, and/or incorporated into a band configured to be worn around the patient's chest or a necklace configured to be worn around the patient's neck. This positioning of external-unit coil 102 provides high transmission efficiency, because the respective axes of external-unit coil 102 and prosthetic-valve coil 36 are generally aligned.

For some applications, prosthetic-aortic-valve control circuitry 40 is configured to use the received energy to drive the one or more electrodes 34 to perform pacing post-implantation, e.g., for several months. Such pacing may employ any standard pacing protocol. For some applications, the pacing is VVI pacing, which is only applied when a QRS complex is not sensed in the ventricle. Alternatively, external-unit control circuitry 104 is configured to drive the one or more electrodes 34 to apply the pacing signal; in this configuration, prosthetic-aortic-valve control circuitry 40, if even provided, is generally passive, i.e., external-unit control circuitry 104 sets the parameters of the pacing signal.

Alternatively, for some applications, prosthetic-aortic-valve control circuitry 40 is configured to (a) use the one or more electrodes 34 to sense a cardiac signal, and (b) drive prosthetic-valve coil 36 to transmit a wireless signal indicative of the sensed cardiac signal. For some applications, the cardiac sensing is performed using techniques described in U.S. Pat. No. 9,005,106 to Gross et al., which is incorporated herein by reference. In these applications, the one or more electrodes 34 are typically not used to apply pacing, any thus need not be configured as a cathode and an anode. Such sensing may enable early discharge of the patient from the hospital after implantation of prosthetic aortic valve 20, before the possible development of left bundle branch block (LBBB). If LBBB develops, as it does in approximately 20-30% of patients, the LBBB is detected by the sensing, an alert is generated, and the LBBB may be treated as appropriate.

Figure 5:
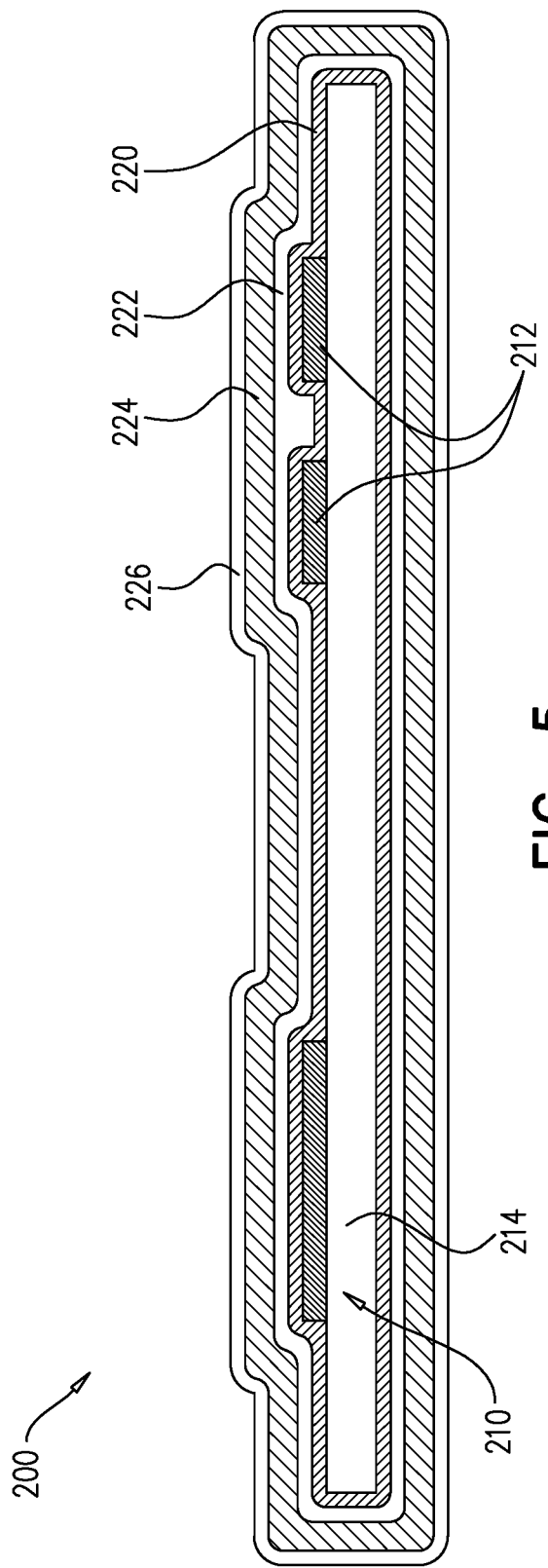
FIG. 5 is a schematic illustration of an electronic implant, in accordance with an application of the present invention.

Reference is now made to FIG. 5, which is a schematic illustration of an electronic implant 200, in accordance with an application of the present invention. Prosthetic-aortic-valve control circuitry 40, described hereinabove with reference to FIGS. 1A-2, may implement features of electronic implant 200.

Electronic implant 200 comprises circuitry 210, which comprises electronic components 212, typically mounted on a long and flexible printed circuit board (PCB) 214. Electronic implant 200 further comprises a multi-layer protective coating, which comprises the following layers in the following order:

a first inner aluminum oxide (AlOx) film layer 220 deposited on circuitry 210, e.g., using atomic layer deposition (ALD);

a second parylene layer 222 deposited (typically, vapor-deposited in a vacuum) on first inner AlOx film layer 220; second parylene layer 222 provides chemical protection for circuitry 210;

optionally, a third layer 224 disposed (typically cast onto) on second parylene layer 222, the third layer, for example, comprising a polymer, such as a polymer selected from the group consisting of: silicone and PTFE; third layer 224 typically has a thickness of between 100 and 200 microns, and is configured to provide mechanical protection for circuitry 210; and optionally, a fourth outer parylene layer 226 deposited (typically, vapor-deposited in a vacuum) on third layer 224; fourth outer parylene layer 226 provides chemical protection for circuitry 210 and third layer 224.

Electronic implant 200 and the layers are drawn highly schematically in FIG. 5, and are not drawn to scale; in particular, the layers are actually much thinner than shown, and the relative thicknesses are different from those shown.

Typically, circuitry 210 is not encased in a case, but is only coated with layers, as described above. A "case" is an enclosure, typically comprising glass and/or metal, that has a structure before circuitry is disposed therein; by contrast, a coating takes the shape of the circuitry to which the coating is applied. By contrast, encasement in a case is standard in the field of implantable circuitry. The lack of such a case allows electronic implant 200 to be thin and flexible, with the tradeoff of shorter lifespan. For prosthetic-aortic-valve control circuitry 40, the shorter lifespan is generally not an issue, because prosthetic-aortic-valve control circuitry 40 is typically only used for several months.

For applications in which prosthetic-aortic-valve control circuit 40 implements features of electronic implant 200, the one or more electrodes 34 are masked during application of the coatings. Thus, prosthetic-aortic-valve control circuitry 40, the one or more elongate insulated electrical conductors 38 (e.g., wires), and prosthetic-valve coil 36 are all coated in the same coating procedure.

The techniques described herein for prosthetic aortic valve 20 may be alternatively used, mutatis mutandis, for non-aortic prosthetic valves, such as prosthetic mitral or tricuspid valves.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A valve prosthesis system comprising:
   (i) a prosthetic aortic valve, which comprises:
      (a) a plurality of prosthetic leaflets;
      (b) a frame;
      (c) a cathode and an anode, which are mechanically coupled to the frame; and
      (d) a prosthetic-valve coil, which is in non-wireless electrical communication with the cathode and the anode; and
   (ii) a non-implantable unit, which comprises:
      (a) an energy-transmission coil; and
      (b) non-implantable control circuitry, which is configured to drive the cathode and the anode to apply a pacing signal and to set parameters of the pacing signal, by wirelessly transferring energy from the energy-transmission coil to the prosthetic-valve coil by inductive coupling.

2. The valve prosthesis system according to claim 1, wherein the prosthetic aortic valve comprises one or more elongate insulated electrical conductors, which directly couple the prosthetic-valve coil in the non-wireless electrical communication with the cathode and the anode.

3. The valve prosthesis system according to claim 1, wherein respective non-electrically-insulated end portions of the prosthetic-valve coil define the cathode and the anode.

4. The valve prosthesis system according to claim 1, wherein the non-implantable control circuitry is configured to set an amplitude of the pacing signal by modulating an amplitude of the energy wirelessly transferred from the energy-transmission coil to the prosthetic-valve coil.

5. The valve prosthesis system according to claim 1, wherein the pacing signal includes pulses, and wherein the non-implantable control circuitry is configured to drive the cathode and the anode to (a) begin application of each pulse of the pacing signal by beginning wirelessly transferring energy from the energy-transmission coil to the prosthetic-valve coil, and (b) conclude the application of each pulse of the pacing signal by ceasing wirelessly transferring energy from the energy-transmission coil to the prosthetic-valve coil.

6. The valve prosthesis system according to claim 1,
   wherein the frame is shaped so as to define: (1) an upstream inflow portion, (2) a downstream outflow portion, and (3) a constriction portion, which is axially between the upstream inflow portion and the downstream outflow portion, wherein the prosthetic leaflets are coupled to the constriction portion, and
   wherein the cathode is mechanically coupled to the upstream inflow portion of the frame.

7. The valve prosthesis system according to claim 6, wherein the prosthetic-valve coil is disposed axially along the downstream outflow portion of the frame.

8. The valve prosthesis system according to claim 1, wherein the cathode and the anode are disposed on the frame such that there is at least 15 mm between the cathode and the anode, when the prosthetic aortic valve is in an expanded fully-deployed configuration, the 15 mm measured along a central longitudinal axis of the frame when in the expanded fully-deployed configuration.

9. The valve prosthesis system according to claim 1, wherein the non-implantable unit is an external unit, which is configured to be disposed outside a body of a subject in which the prosthetic aortic valve is disposed.

10. The valve prosthesis system according to claim 1,
   wherein the non-implantable unit is a delivery system, which further comprises a delivery tube, and one or more wires, which pass along the delivery tube,
   wherein the energy-transmission coil is a delivery-system coil,
   wherein the non-implantable control circuitry is delivery-system control circuitry, which is in electrical communication with the delivery-system coil via the one or more wires, and wherein the delivery-system coil is coupled to the delivery tube at a distal site of the delivery tube.

11. The valve prosthesis system according to claim 10, wherein the delivery-system control circuitry is configured to drive the cathode and the anode to apply rapid ventricular pacing, by wirelessly transferring the energy from the delivery-system coil to the prosthetic-valve coil by inductive coupling.

12. The valve prosthesis system according to claim 10, wherein the prosthetic aortic valve is (i) removably disposable in the delivery tube in a compressed delivery configuration and (ii) configured to assume:
   (A) a partially-expanded partially-deployed configuration upon being partially released from a distal end of the delivery tube such that (1) at least the cathode is positioned outside the delivery tube, and (2) the prosthetic-valve coil is compressed within the delivery tube, and
   (B) an expanded fully-deployed configuration upon being fully released from the distal end of the delivery tube, and
   wherein the delivery-system control circuitry is configured to drive the cathode and the anode to apply the pacing signal and to set the parameters of the pacing signal, by wirelessly transferring the energy from the delivery-system coil to the prosthetic-valve coil at least when the prosthetic aortic valve is in the partially-deployed configuration.

13. The valve prosthesis system according to claim 12, further comprising an external unit, which is configured to be disposed outside a body of a subject in which the prosthetic aortic valve is disposed, and which comprises:
   an external-unit coil; and
   external-unit control circuitry, which is configured to drive the external-unit coil to drive the cathode and the anode to apply the pacing signal and to set the parameters of the pacing signal, by wirelessly transferring energy, by inductive coupling, to the prosthetic-valve coil when the prosthetic aortic valve is in the expanded fully-deployed configuration.

14. A method comprising:
   deploying, via vasculature of a patient, a prosthetic aortic valve of a valve prosthesis system in an aortic valve annulus, the prosthetic aortic valve including (a) a plurality of prosthetic leaflets, (b) a frame, (c) a cathode and an anode, which are mechanically coupled to the frame, and (d) a prosthetic-valve coil, which is in non-wireless electrical communication with the cathode and the anode; and
   activating non-implantable control circuitry of a non-implantable unit of the valve prosthesis system to drive the cathode and the anode to apply a pacing signal and to set parameters of the pacing signal, by wirelessly transferring energy from an energy-transmission coil of the non-implantable unit to the prosthetic-valve coil by inductive coupling.

15. The method according to claim 14, wherein activating the non-implantable control circuitry to drive the cathode and the anode to apply the pacing signal comprises activating the non-implantable control circuitry to set an amplitude of the pacing signal by modulating an amplitude of the energy wirelessly transferred from the energy-transmission coil to the prosthetic-valve coil.

16. The method according to claim 14, wherein the pacing signal includes pulses, and wherein activating the non-implantable control circuitry to drive the cathode and the anode to apply the pacing signal comprises activating the non-implantable control circuitry to drive the cathode and the anode to (a) begin application of each pulse of the pacing signal by beginning wirelessly transferring energy from the energy-transmission coil to the prosthetic-valve coil, and (b) conclude the application of each pulse of the pacing signal by ceasing wirelessly transferring energy from the energy-transmission coil to the prosthetic-valve coil.

17. The method according to claim 14, wherein the non-implantable unit is an external unit, which is disposed outside a body of a subject in which the prosthetic aortic valve is disposed.

18. The method according to claim 14,
   wherein the non-implantable unit is a delivery system of the valve prosthesis system, and the energy-transmission coil is a delivery-system coil that is coupled to a delivery tube of the delivery system at a distal site of the delivery tube,
   wherein the non-implantable control circuitry is delivery-system control circuitry, which is in electrical communication with the delivery-system coil via one or more wires that pass along the delivery tube,
   wherein deploying the prosthetic aortic valve comprises:
      advancing the delivery tube through the vasculature until a distal end of the delivery tube is disposed in an ascending aorta of the patient, while the prosthetic aortic valve is removably disposed in the delivery tube in a compressed delivery configuration; and
      partially releasing the prosthetic aortic valve from the distal end of the delivery tube such that the prosthetic aortic valve assumes a partially-expanded partially-deployed configuration, in which (a) at least the cathode is positioned outside the delivery tube, and (b) the prosthetic-valve coil is compressed within the delivery tube;
   wherein activating the non-implantable control circuitry comprises, after partially releasing the prosthetic aortic valve from the distal end of the delivery tube, activating the delivery-system control circuitry to drive the cathode and the anode to apply the pacing signal and to set the parameters of the pacing signal, by wirelessly transferring energy from the delivery-system coil to the prosthetic-valve coil by inductive coupling at least when the prosthetic aortic valve is in the partially-deployed configuration, and
   wherein deploying the prosthetic aortic valve further comprises, after activating the delivery-system control circuitry, fully releasing the prosthetic aortic valve from the distal end of the delivery tube such that the prosthetic aortic valve assumes an expanded fully-deployed configuration.

19. The method according to claim 18, wherein activating the delivery-system control circuitry comprises activating the delivery-system control circuitry to drive the cathode and the anode to apply rapid ventricular pacing, by wirelessly transferring the energy from the delivery-system coil to the prosthetic-valve coil by inductive coupling at least when the prosthetic aortic valve is in the partially-deployed configuration.

20. The method according to claim 18, further comprising, after fully releasing the prosthetic aortic valve from the distal end of the delivery tube, activating external-unit control circuitry of an external unit to drive an external-unit coil of the external unit to drive the cathode and the anode to apply the pacing signal and to set the parameters of the pacing signal, by wirelessly transferring energy, by inductive coupling, to the prosthetic-valve coil when the prosthetic aortic valve is in the expanded fully-deployed configuration, wherein the external unit is disposed outside a body of a subject in which the prosthetic aortic valve is disposed.

21. The method according to claim 18, wherein the delivery-system control circuitry is configured to cease driving the delivery-system coil to drive the cathode and the anode when the prosthetic aortic valve assumes the expanded fully-deployed configuration upon being fully released from the distal end of the delivery tube.

22. The method according to claim 18, wherein partially releasing the prosthetic aortic valve from the distal end of the delivery tube comprises positioning the cathode adjacent to cardiac tissue near the bundle of His.

* * * * *